United States Patent [19]

Chauvette et al.

[11] 3,992,377

[45] Nov. 16, 1976

[54] 3-THIO-SUBSTITUTED CEPHALOSPORIN ANTIBIOTICS

[75] Inventors: Robert R. Chauvette; Gary A. Koppel, both of Indianapolis, Ind.

[73] Assignee: Eli Lilly and Company, Indianapolis, Ind.

[22] Filed: Dec. 13, 1974

[21] Appl. No.: 532,431

[52] U.S. Cl. .............................. 260/243 C; 424/246
[51] Int. Cl.$^2$ ....................................... C07D 501/16
[58] Field of Search ................................ 260/243 C

[56] References Cited
UNITED STATES PATENTS
3,641,021   2/1972   Ryan et al. .................... 260/243 C

OTHER PUBLICATIONS

Scartazzini et al., Chemical Abstracts 80, 83,018n (1974).
Scartazzini et al., Chemical Abstracts 80, 83,019p (1974).

*Primary Examiner*—Nicholas S. Rizzo
*Assistant Examiner*—Diana G. Rivers
*Attorney, Agent, or Firm*—William B. Scanlon; Everet F. Smith

[57] ABSTRACT

7-Acylamido-3-cephem-4-carboxylic acid antibiotics directly substituted in the 3-position of the cephem ring system with a sulfur atom bonded to a 5- or 6-membered heterocyclic ring, a lower alkyl group, or a phenyl or substituted phenyl group are prepared with the corresponding 3-halo-3-cephem esters. For example, p-nitrobenzyl 7-[2-(2-thienyl)acetamido]-3-chloro-3-cephem-4-carboxylate reacts with 1-methyl-1H-tetrazol-5-ylthiol to provide p-nitrobenzyl 7-[2-(2-thienyl)acetamido]-3-[(1-methyl-1H-tetrazol-5-yl)thio]-3-cephem-4-carboxylate. The p-nitrobenzyl ester group is removed by catalytic hydrogenolysis to provide the antibiotic carboxylic acid compound. Alternatively, the antibiotics are prepared by reacting a 3-alkylsulfonyloxy, or 3-arylsulfonyloxy-3-cephem, for example, 3-methanesulfonyloxy-3-cephem, or a 3-p-toluenesulfonyloxy-3-cephem with the heterocyclic thiol, the phenyl or substituted phenylthiol, or with the lower alkylthiol.

13 Claims, No Drawings

3-THIO-SUBSTITUTED CEPHALOSPORIN ANTIBIOTICS

BACKGROUND OF THE INVENTION

This invention relates to cephalosporin antibiotics. In particular it relates to cephalosporin antibiotics directly substituted in the 3-position of the cephem ring system with a divalent sulfur atom also bonded to a 5- or 6-membered heterocyclic ring, a $C_1$ to $C_4$ lower alkyl group, or with a phenyl or substituted phenyl group.

Since the discovery of cephalosporin C as well as the further discovery that the α-amino adipoyl side chain thereof could be cleaved to provide the cephalosporin nucleus, a large number of different cephalosporin antibiotics have been synthesized and described. In these syntheses, a large number of structural variations have been made in the 7-position side chain by the acylation of the 7-amino cephalosporin nucleus. Many other variations, and oftentimes in combination with variations in the side chain, have been made in the 3'-position of the cephalosporin nucleus. For example, the acetoxy group of the acetoxymethyl substituent in the 3-position of the cephalosporin nucleus has been substituted by a wide variety of groups such as the preparation of the $C_4$ compounds with pyridines, the displacement of the acetoxy group with sulfur nucleophiles as well as with other groups.

Cephalosporin antibiotics having a methyl group in the 3-position of the cephem ring, the deacetoxycephalosporanic acids, have been synthesized by the now well known penicillin sulfoxide rearrangement discovered by R. B. Morin, et al., U.S. Pat. No. 3,275,626. Until recently, all of the known cephalosporin antibiotics possessed the structural feature of either a 3-methyl group, a substituted 3-methyl group or a hydrogen at the 3-position of the cephem ring system. Recently, however, R. R. Chauvette, J. Org. Chem. 38, 2994 (1973) and J. Amer. Chem. Soc. 96, 4986 (1974), described a process for the preparation of 3-exomethylenecepham compounds and their conversion to 3-hydroxy, 3-methoxy, and 3-halo-3-cephem compounds wherein the substituent group was bonded directly to the carbon in the 3-position of the cephem ring system. Thus, a new class of cephalosporin antibiotics are now known.

As mentioned above, many cephalosporin antibiotics are known wherein the acetoxy group of the acetoxymethyl substituent in the 3-position of the cephalosporanic acid is displaced with a sulfur nucleophile. Exemplary of these compounds are those described by Takano et al. in U.S. Pat. No. 3,516,997, by Ryan in U.S. Pat. No. 3,641,021, and by Clark et al., in U.S. Pat. No. 3,688,203. All of these antibiotics, however, bear the traditional substitution pattern of the cephalosporin antibiotics wherein a methylene group is interposed between the cephem ring and the displacing or substituting group.

DETAILED DESCRIPTION

The 3-thiosubstituted cephalosporin antibiotics of this invention are represented by the following structural formula,

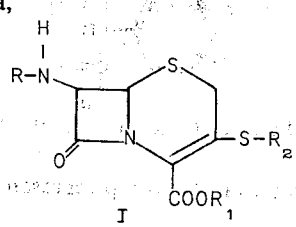

wherein R is hydrogen or an acyl group derived from a carboxylic acid and represented by the formula

wherein R' is $C_1$-$C_6$ alkyl, $C_1$-$C_3$ haloalkyl, $C_1$-$C_3$ cyanoalkyl, phenyl, methylphenyl, hydroxyphenyl, halophenyl, nitrophenyl, aminophenyl, and methoxyphenyl;

or R' is a group of the formula

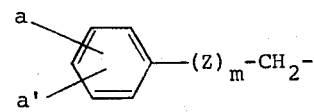

wherein $a$ and $a'$ independently are hydrogen, $C_1$-$C_4$ lower alkyl, $C_1$-$C_4$ lower alkoxy, halogen, hydroxy, nitro, amino, or carboxy;

Z is O or S; and $m$ is 0 or 1;

or R' is a group of the formula

wherein P is 2-thienyl, 3-thienyl, phenyl or a substituted phenyl group of the formula

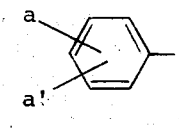

wherein $a$ and $a'$ are as defined above,

Q is hydroxyl, formyloxy, acetoxy, carboxy, sulfo, amino, or amino protected by t-butyloxycarbonyl, 2,2,2-trichlorethoxycarbonyl, or the group of the formula

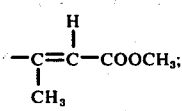

or R' is a group of the formula

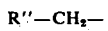

wherein R'' is a 2-thienyl, 3-thienyl, 2-furyl, 2-oxazolyl, 2-thiazolyl, or 1-tetrazolyl;

$R_1$ is hydrogen, benzyl, 4-methoxybenzyl, 4-nitrobenzyl, diphenylmethyl, 2,2,2-trichloroethyl, or t-butyl;

$R_2$ is $C_1$-$C_4$ alkyl, phenyl, or a substituted phenyl group of the formula

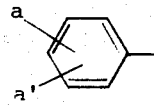

wherein a and a' have the same meanings as defined above,
or R$_2$ is a heterocyclic ring selected from the group consisting of

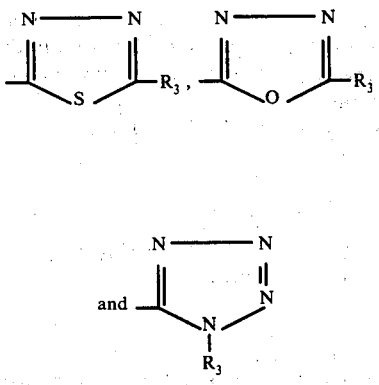

wherein R$_3$ is C$_1$-C$_3$ lower alkyl;
and when R$_1$ is hydrogen, the pharmaceutically acceptable non-toxic salts thereof.

In the foregoing definition of the compounds provided by this invention the term "C$_1$-C$_6$ alkyl" refers to the straight and branched chain alkyl hydrocarbon groups such as methyl, ethyl, n-propyl, iso-propyl, n-butyl, sec-butyl, n-amyl, isoamyl, n-hexyl, and the like; "C$_1$-C$_3$ cyanoalkyl" refers to such groups as cyanomethyl, 2-cyanoethyl, 3-cyanopropyl, and 2-cyanopropyl; "C$_2$-C$_4$ alkanoyl" refers to acetyl, propionyl, butyryl, and the like; "C$_1$-C$_3$ haloalkyl" refers to chloromethyl, bromomethyl, 2-chloroethyl, 3-bromopropyl and the like; "C$_1$-C$_4$ lower alkyl" refers to the straight and branched chain lower alkyl hydrocarbon groups such as methyl, ethyl, n-propyl, iso-propyl, n-butyl, t-butyl, and the like; "C$_1$-C$_4$ lower alkoxy" refers to methoxy, ethoxy, iso-propoxy, n-butoxy, and the like. As used herein the term "halogen" refers to fluoro, chloro, bromo, and iodo. The term "halophenyl" refers to the chloro and bromo substituted phenyl groups such as 4-chlorophenyl, 4-bromophenyl, 2,4-dichlorophenyl, and the like.

Illustrative of the groups in the above definition represented by the following formula where m is O are

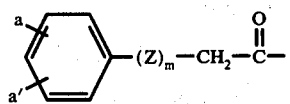

phenylacetyl, 4-methylphenylacetyl, 3-ethylphenylacetyl, 4-isopropylphenylacetyl, 2-methylphenylacetyl, 4-chlorophenylacetyl, 4-nitrophenylacetyl, 4-bromophenylacetyl, 2,4-dichlorophenylacetyl, 3-bromophenylacetyl, 4-iodophenylacetyl, 2-fluorophenylacetyl, 3,4-dihydroxyphenylacetyl, 4-hydroxyphenylacetyl, 3-hydroxyphenylacetyl, 2,6-dimethoxyphenylacetyl, 3-carboxyphenylacetyl, 4-aminophenylacetyl, 3-ethoxyphenylacetyl, 4-methoxyphenylacetyl, 3,4-dimethoxyphenylacetyl, 4-t-butoxyphenylacetyl, 2-carboxyphenylacetyl, 3-chloro-4-methylphenylacetyl, 3-nitrophenylacetyl, and the like. When in the above formula m = 1 and Z represents —O—, illustrative groups are the following. Phenoxyacetyl, 4-hydroxyphenoxyacetyl, 3-hydroxyphenoxyacetyl 4-chlorophenoxyacetyl, 3-bromophenoxyacetyl, 3-ethylphenoxyacetyl, 4-methylphenoxyacetyl, 3-hydroxy-3-methylphenoxyacetyl, 4-aminophenoxyacetyl, 3-nitrophenoxyacetyl, 2-carboxyphenoxyacetyl, 2-chlorophenoxyacetyl, 4-t-butylphenoxyacetyl, 4-methoxyphenoxyacetyl, 3,4-dimethoxyphenoxyacetyl, 2-aminophenoxyacetyl, 4-isopropoxyphenoxyacetyl, 4-nitrophenoxyacetyl, and like acyl groups. When in the foregoing formula m = 1 and Z represents —S—, illustrative groups are the following. Phenylmercaptoacetyl, 4-chlorophenylmercaptoacetyl, 3-hydroxyphenylmercaptoacetyl, 3,4-dimethylphenylmercaptoacetyl, 4-aminophenylmercaptoacetyl, 3,4-dichlorophenylmercaptoacetyl, 3-bromophenylmercaptoacetyl, 4-fluorophenylmercaptoacetyl, 2,6-difluorophenylmercaptoacetyl, 4-nitrophenylmercaptoacetyl, 3-fluorophenylmercaptoacetyl, and like groups.

When in formula I R' represents a group of the formula

illustrative acyl groups,

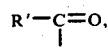

are the mandeloyl group of the formula

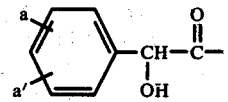

the O-formyl derivative thereof represented by the following formula

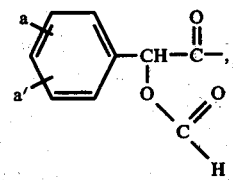

the α-carboxyphenylacetyl group represented by the following formula

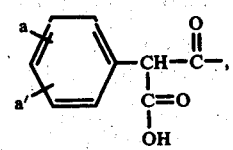

the α-sulfophenylacetyl group represented by the formula

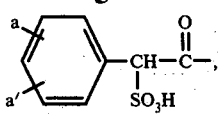

as well as those 2-thienyl and 3-thienyl acyl groups where in the above formula the phenyl group is replaced with a 2-thienyl or 3-thienyl ring, the D-phenylglycyl group represented by the formula

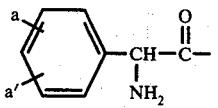

as well as the 2- and 3-thienylglycyl groups represented by the formulas

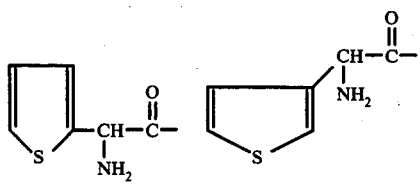

Illustrative of the foregoing acyl groups are 4-methylmandeloyl, 4-hydroxymandeloyl, 3-hydroxymandeloyl, 4-aminomandeloyl, 3-bromomandeloyl, 4-chloromandeloyl, 3-methyl-4-fluoromandeloyl, 2-fluoromandeloyl, 4-fluoromandeloyl, 4-methoxymandeloyl, 3,4-dimethyl-O-formylmandeloyl, 4-chloro-O-formylmandeloyl, 3-amino-O-formylmandeloyl, 3-bromo-O-formylmandeloyl, 3,4-dimethoxy-O-formylmandeloyl, O-acetyl mandeloyl, O-acetyl 4-hydroxymandeloyl, α-carboxy-4-methylphenylacetyl, α-carboxy-3,4-dichlorophenylacetyl, α-carboxy-4-hydroxyphenylacetyl, α-carboxy-2-methoxyphenylacetyl, α-carboxy-4-isopropoxyphenylacetyl, α-carboxy-3-hydroxyphenylacetyl, α-carboxy-4-aminophenylacetyl, α-sulfo-4-methylphenylacetyl, α-sulfo-3,4-dichlorophenylacetyl, α-sulfo-4-chlorophenylacetyl, α-sulfo-4-hydroxyphenylacetyl, α-sulfo-3-methoxyphenylacetyl, α-carboxy-2-thienylacetyl, α-carboxy-3-thienylacetyl, α-hydroxy-2-thienylacetyl, α-hydroxy-3-thienylacetyl, α-sulfo-2-thienylacetyl, α-formyloxy-2thienylacetyl, α-acetoxy-2-thienylacetyl, α-amino-2-thienylacetyl, α-amino-3-thienylacetyl, α-amino-2-furylacetyl, D-α-aminophenylacetyl(D-phenylglycine), D-α-amino-4-hydroxyphenylacetyl, D-α-amino-3-hydroxyphenylacetyl, D-α-amino-3-chloro-4-hydroxyphenylacetyl, and D-α-amino-4-chlorophenylacetyl.

When in the foregoing formula R' represents a group of the formula R''—CH₂—, illustrative of the acyl groups of the formula I are the following: 2-thienylacetyl, 3-thienylacetyl, 2-furylacetyl, oxazolyl-2-acetyl, thiazolyl-2-acetyl, and the tetrazolyl-1-acetyl group represented by the following formula

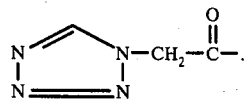

Illustrative of the groups represented by the 3-thio substituent, —S—R₂, when R₂ is C₁-C₄ alkyl, are such groups as methylthio, ethylthio, iso-propylthio, n-butylthio, sec-butylthio, and the like; and when R₂ represents phenyl or a substituted phenyl, —SR₂ can be phenylthio, 4-methylphenylthio, 4-iso-propylphenylthio, 4-t-butylphenylthio, 3,4-dimethylphenylthio, 4-ethoxyphenylthio, 3-methoxyphenylthio, 2-methoxyphenylthio, 3- or 4-nitrophenylthio; the halo substituted phenylthio groups such as 2-chlorophenylthio, 4-chlorophenylthio, 3,4-dichlorophenylthio, 3-bromophenylthio; 4-fluorophenylthio, 3-fluorophenylthio; the hydroxyphenylthio groups such as 4-hydroxyphenylthio, 3,5-dichloro-4-hydroxyphenylthio, 3-chloro-4-hydroxyphenylthio, 4-methyl-3-hydroxyphenylthio; the amino substituted phenylthio groups such as 3- or 4-aminophenylthio; the carboxy substituted phenylthio groups such as 4-carboxyphenylthio, 3-carboxyphenylthio, as well as the alkali metal salt forms thereof and like substituted phenylthio groups.

When R₂ represents a heterocyclic ring illustrative of the 3-thio substituent groups —S—R₂ are the 5-lower alkyl substituted oxa or thiadiazole-2-ylthio groups such as 5-methyl-1,3,4-oxadiazole-2-ylthio, 5-methyl-1,3,4-thiadiazole-2-ylthio, 5-ethyl-1,3,4-thiadiazole-2-ylthio, 5-iso-propyl-1,3,4-thiadiazole-2-ylthio, 5-n-propyl-1,3,4-oxadiazole-2-ylthio, and the like; the substitued tetrazole groups such as 1-methyl-1H-tetrazole-5-ylthio, 1-ethyl-1H-tetrazole-5-ylthio, 1-isopropyl-1H-tetrazole-5-ylthio, and the like.

A preferred group of compounds represented by the formula I are those represented by the following formula II.

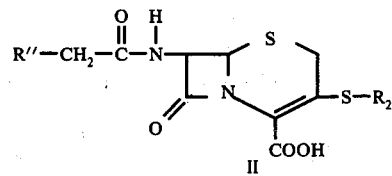

wherein R'' represents 2-thienyl, 3-thienyl, 2-furyl, and 1-tetrazyl, and R₂ is C₁-C₄ alkyl, or a heterocyclic ring selected from among

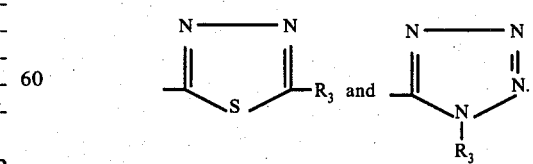

Illustrative of these compounds are:
7-(2-thienylacetamido)-3-methylthio-3-cephem-4-carboxylic acid, 7-(2-thienylacetamido)-3-(5-methyl-1,3,4-thiadiazole-2-ylthio)-3-cephem-4-carboxylic acid, 7-(2-thienylacetamido)-3-(1-methyl-1H-tetrazole-5-ylthio)-3-cephem-4-carboxylic acid, 7-(2-furylacetamido)-3-(1-methyl-1H-tetrazole-5-ylthio)-3-cephem-4-carboxylic acid, 7(1-tetrazolylacetamido)-3-(5-methyl-1,3,4-oxadiazole-2-ylthio)-3-cephem-4-carboxylic acid, and the pharmaceutically effective non-toxic salts thereof.

A further preferred group of compounds represented by the formula I are those represented by the following formula III.

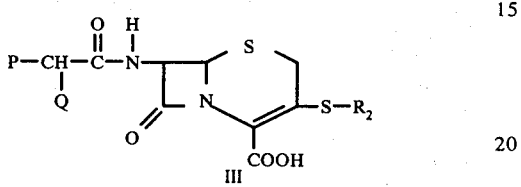

wherein P represents phenyl or a substituted phenyl group as defined in formula I and Q is hydroxy or amino, and $R_2$ is $C_1$-$C_4$ alkyl or a heterocyclic group selected from

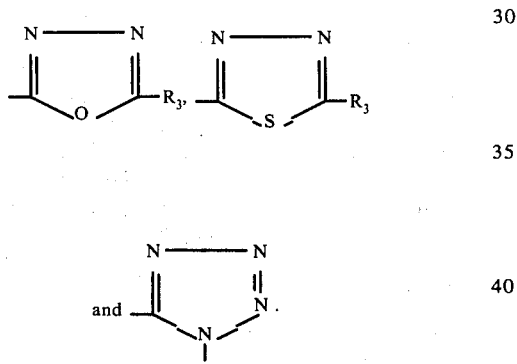

An especially preferred group of compounds provided herein are those represented where in the above formula III $R_2$ is the 1-methyl-1H-tetrazole-5-ylthio group and Q is amino or hydroxy, namely, 7-(D-phenylglycylamido)-3-(1-methyl-1H-tetrazole-5-ylthio)-3-cephem-4-carboxylic acid, the zwitterionic form thereof, the pharmaceutically acceptable carboxylic acid salts and the acid addition salts formed with the basic α-amino group thereof; and 7-(D-mandelamido)-3-(1-methyl-1H-tetrazole-5-ylthio)-3-cephem-4-carboxylic acid and the pharmaceutically acceptable salts thereof formed with the carboxylic acid.

The cephalosporin antibiotics of this invention are represented by the above formula I and are prepared by reacting a 3-halo-3-cephem ester or a 3-alkylsulfonyloxy-3-cephem ester, or a 3-phenyl or substituted phenylsulfonyloxy-3-cephem ester with a lower alkyl mercaptan, a thiophenol or a substituted thiophenol, or a 5-lower alkyl-1,3,4-oxa or thiadiazol-2-thiol, or with a 1-lower alkyl-1H-tetrazol-5-thiol. The following generalized reaction scheme illustrates the preparation of the compounds of this invention.

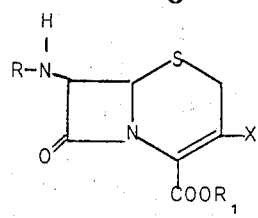

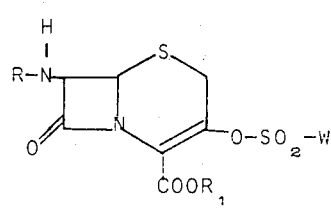

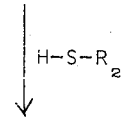

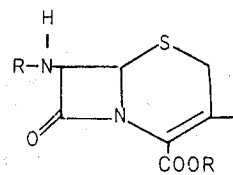

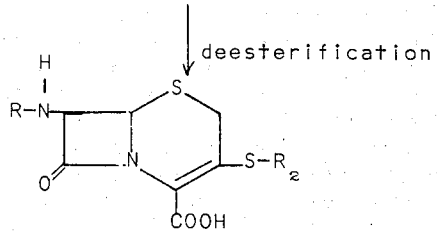

In the above reaction scheme, R, $R_1$, and $R_2$ have the same meanings as defined in the formula I, X is chloro or bromo, and W represents $C_1$-$C_3$ alkyl, phenyl, halophenyl, $C_1$-$C_3$ lower alkylphenyl, or nitrophenyl.

In preparing the 3-thio substituted 3-cephem compounds of this invention, a 7-acylamido-3-halo-(or sulfonyloxy-)3-cephem-4-carboxylic acid ester is reacted in an inert solvent with at least an equimolar amount of the thiol compound, H—S—$R_2$, a lower alkyl mercaptan, thiophenol or a substituted thiophenol, a 5-lower alkyl substituted 1,3,4-oxa or thiadiazol-2-thiol, or a 1-lower alkyl substituted-1H-tetrazol-5-thiol, in the presence of a suitable base, for example sodium hydride, or sodium bisulfite. When the reaction is carried out with the aid of a base such as sodium hydride, the reaction is carried out at a temperature between about −60° and −25° C. or when a somewhat weaker base is employed in the reaction, the reaction can be carried out at about 0° to 30° C.

Solvents which may be employed depend upon the nature of the base and the nature of the reactant used in the synthesis. Dimethylformamide (DMF) and dimethylacetamide (DMAc) are effective solvents in the reaction employing sodium hydride at the colder temperatures. Dimethylsulfoxide can also be employed in the reaction and is a preferred solvent when sodium bisulfite is used.

The reaction is carried out under anhydrous conditions. The solvent employed, for example dimethylsulfoxide (DMSO), is best dried for use in the reaction by a molecular sieve.

The compounds of the formula I wherein $R_2$ is a $C_1$–$C_4$ lower alkyl group or a phenyl or substituted phenyl group are preferably prepared at the lower temperatures when sodium hydride is employed as the base. The preparation of the compounds wherein $R_2$ is a thiadiazole, oxadiazole, or tetrazole heterocyclic ring are preferably prepared at or about room temperature and with sodium bisulfite.

In carrying out the reaction at the warmer temperatures, i.e., at or about 0° to 30° C., some isomerization of the double bond in the cephem ring system occurs. The isomerization is minimized by the use of a weak base such as sodium bisulfite. The product, a mixture of the $\Delta^2$ and $\Delta^3$ cephem 3-thio substituted compounds can be separated; however, it is more convenient to convert the $\Delta^2$ isomer to the desired $\Delta^3$ isomer. This is accomplished by the known method which comprises oxidation of the $\Delta^2$ cephem to the sulfoxide with a peracid such as m-chloroperbenzoic acid. During the formation of the sulfoxide, the $\Delta^2$ double bond migrates to the $\Delta^3$ position. The $\Delta^3$ sulfoxide is then reduced by the known method by employing phosphorus trichloride in an inert solvent to obtain the desired $\Delta^3$ cephem esters.

Following the preparation of the 3-thio substituted 3-cephem esters as described above, the ester group is removed by deesterification to provide the antibiotic compound of the invention as the free acid.

In a specific example of the method employed for the preparation of the compounds of the invention, the p-nitrobenzyl ester of 7-[2-(2-thienyl)acetamido]-3-p-toluenesulfonyloxy-3-cephem-4-carboxylate is dissolved in dimethylformamide and the solution cooled to about −40° C. in an acetone dry ice bath. To the cold solution is added an equimolar amount of methyl mercaptan in dimethylformamide containing sodium hydride. The cold reaction mixture is stirred for about one to about two hours and is then acidified by the addition of glacial acetic acid. The reaction mixture is then warmed to room temperature and is evaporated and the residue extracted with an organic solvent such as ethyl acetate. The extract is washed wih water, brine, and with dilute hydrochloric acid. The washed extract is dried and evaporated to yield the reaction product. The product can be further purified by recrystallization from a suitable solvent or by chromatography, for example preparative thin layer chromatography or when larger quantities of compound are involved by column chromatography over silica gel. The p-nitrobenzyl ester is removed to obtain the free acid form of the antibiotic by catalytic hydrogenolysis carried out as follows. The ester is dissolved in an inert solvent, for example, tetrahydrofuran, dioxane, or a lower alcohol such as methanol or ethanol, or mixtures thereof, and a catalytic amount of 5 percent palladium on carbon is added. The mixture is then hydrogenated at about 50 lbs. per square inch at room temperature to provide the product, 7-[2-(2-thienyl)acetamido]-3-methylthio-3-cephem-4-carboxylic acid.

In another specific example of the preparation of the compound described above, p-nitrobenzyl 7-[2-(2-thienyl)acetamido]-3-chloro-3-cephem-4-carboxylate is dissolved in dry dimethyl sulfoxide and an equimolar amount of 1-methyl-1H-tetrazole-5-thiol is added to the solution. The solution is maintained at room temperature while a 4 molar excess of sodium bisulfite is added in four equal portions at hourly intervals. The reaction mixture is stirred at room temperature for 5 hours and is then poured into a mixture of water and a water immiscible solvent such as ethyl acetate. The organic layer containing the reaction product is separated and is washed and dried. The dried extract is evaporated and the amorphous residue triturated with diethyl ether. The product containing a mixture of the $\Delta^2$ and $\Delta^3$ cephem is chromatographed over a column packed with silica gel to further purify the product.

The isomeric mixture is suspended or dissolved in an inert solvent and is cooled to ice bath temperature. m-Chlorobenzoic acid is added in excess to the cold suspension or solution. The reaction mixture is allowed to stir in the cold for about 2 to 4 hours and then at room temperature for about 2 hours and is then evaporated to dryness under vacuum. The dry reaction product mixture is dissolved in a mixture of water and a water immiscible solvent such as ethyl acetate. The organic layer is separated and is washed and dried and thereafter evaporated to dryness. The dry product is usually obtained as an amorphous residue and can be obtained crystalline by crystallization from a suitable solvent or oftentimes trituration with diethyl ether. The crystalline, p-nitrobenzyl 7-[2-(2-thienyl)acetamido]-3-[(1-methyl-1H-tetrazole-yl)thiol)-3-cephem-4-carboxylate sulfoxide is then reduced to the $\Delta^3$ cephem sulfide by dissolving the ester in dry dimethylformamide and treating the solution with excess phosphorus trichloride. The mixture is stirred for about 15 minutes and then is poured into a mixture of ethyl acetate and water. The organic phase is separated, washed with water, dried and then evaporated to yield the sulfide ester.

The p-nitrobenzyl ester group is removed from the $\Delta^3$ cephem ester by catalytic hydrogenolysis with 5 percent palladium on carbon at room temperature by the methods known in the art.

In preparing the compounds of the invention, certain starting materials are preferred. In the reaction scheme set forth above, those starting materials wherein X is chloro are preferred among the 3-halo-3-cephem starting materials. When the starting material employed is a 3-cephem-3-sulfonate ester, the methyl sulfonyloxy and the p-toluene sulfonyloxy groups represented when W is methyl and tolyl are preferred. Preferred ester groups are those previously described above, namely the p-nitrobenzyl, the p-methoxybenzyl, the 2,2,2-trichloroethyl, and the diphenylmethyl (benzhydryl) ester groups. These ester groups are preferred because they are easily removed to provide the antibiotic compounds of this invention. The methods for removing these ester groups are known in the art. The p-nitrobenzyl ester group is removed by catalytic hydrogenolysis or with zinc and hydrochloric acid. The trichloroethyl ester group is removed with zinc and formic or acetic acids. The p-methoxybenzyl group and the benzhydryl group can be removed with trifluoroacetic acid in the cold. Those skilled in the art will recognize and appreciate that other readily removable ester groups can be employed in the preparation of the compounds described herein. A wide variety of such ester groups are known in the cephalosporin art and are used in the synthesis of this class of antibiotics.

The preparation of compounds of the formula I wherein R represents a phenylglycine or a thienylglycine side chain, the free amine group in the α-position of the side chain is desirably protected by a suitable amino-protecting group. A wide variety of these protecting groups are known in this art. For example, urethane amino protecting groups such as the t-butyloxycarbonyl group, the cyclopentyloxycarbonyl group, the haloalkoxycarbonyl groups; the enamine protecting groups such as those formed with methyl acetoacetate and other diketones and keto esters, as well as the hydrocarbon protecting groups such as the trityl group. These amino protecting groups serve the function of protecting the amino group during the course of the reactions carried out on other portions of the molecule. The ester groups particularly described here, namely the t-butyloxycarbonyl group, the 2,2,2-trichloroethoxycarbonyl group, and the enamine group formed with ethylacetoacetate or with methylacetoacetate are only exemplary of the wide variety of protecting groups which could be employed.

The lower alkyl mercaptans, the thiophenols and substituted thiophenols are all well known and readily available starting materials. The 5-substituted oxa and thiadiazoles employed in this invention are also known starting materials which are readily prepared. Likewise, the 1-alkyl-1H-tetrazole-5-thiol compounds are known and readily available starting materials.

The compounds of the invention are alternatively prepared by reacting a 7-amino-3-chloro (bromo)-3-cephem-4-carboxylic acid ester (formula I R = H) with the lower alkyl mercaptan, thiophenol or substituted thiophenol, or with the heterocyclic thiol as described above. Following the substitution reaction introducing the thio substituent in the 3-position of the cephem ring, the nucleus thus obtained is then acylated with the desired derivative of a carboxylic acid,

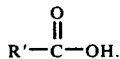

The acylation of the 7-amino-3-thio substituted 3-cephem-4-carboxylic acid esters is carried out by following known acylation procedures. For example, the acid chloride of the desired carboxylic acid acylating agent can be reacted with the nucleus in an inert solvent such as aqueous acetone in the presence of hydrogen halide acceptor such as an inorganic base like sodium bicarbonate or sodium carbonate, or in the presence of an organic amine such as triethylamine or pyridine.

For example, p-nitrobenzyl 7-amino-3-methylthio-3-cephem-4-carboxylate is reacted with phenylacetyl chloride in cold aqueous acetone containing an excess of sodium bicarbonate to provide the acylated compound p-nitrobenzyl 7-phenylacetamido-3-methylthio-3-cephem-4-carboxylate. Similarly, diphenylmethyl 7-amino-3-(1-methyl-1H-tetrazole-5-ylthio)-3-cephem-4-carboxylate is reacted with 2-thienylacetyl chloride in aqueous acetone at a temperature of about 5° to about 10° C. in the presence of sodium bicarbonate to provide the 7-[2-(2-thienyl)acetamido]ester.

Preparation of Starting Materials

As described above, the compounds of this invention are prepared with two different types of starting materials, the 3-halo-3-cephem esters and the 3-alkylsulfonyloxy or phenyl or substituted phenylsulfonyloxy-3-cephem esters. Both types of starting materials are prepared with 7-acylamido-(or 7-amino)3-hydroxy-3-cephem-4-carboxylic acid esters. The 3-hydroxy-3-cephem esters in turn are prepared by the ozonolysis of a 7-acylamido-3-exomethylene cepham ester. The 3-exomethylene cepham compounds are described by R. R. Chauvette et al., *J. Org. Chem.*, 38, 2994 (1973) and in copending application Ser. No. 118,941, filed Feb. 25, 1971 now U.S. Pat. No. 3,932,293, issued Jan. 13, 1976. The ozonolysis of the 3-exomethylenecepham esters and the 3-hydroxy-3-cephem esters obtained thereby are described in copending applications Ser. Nos. 310,190 and 310,191 both filed on Nov. 28, 1972, now U.S. Pat. Nos. 3,917,588, and 3,917,587, respectively, both issued Nov. 4, 1975.

As described therein a 7-acylamido-3-exomethylenecepham-4-carboxylic acid ester or a 7-amino-3-exomethylenecepham-4-carboxylic acid ester is reacted with ozone in an inert solvent at a temperature between −80° and 0° C. to form the ozonide derivative of the 3-exomethylene double bond. The ozonide intermediate, which is not isolated, is decomposed by reacting the ozonide in situ with a mild reducing agent such as sodium bisulfite, or preferably sulfur dioxide, to provide the corresponding 3-hydroxy-3-cephem-4-carboxylic acid ester.

The ozonolysis of a 7-amino-3-exomethylenecepham-4-carboxylic acid ester or a 7-acylamido-3-exomethylenecepham-4-carboxylic acid ester of the following formula IV is carried out by passing ozone through a solution of the 3-exomethylenecepham ester in an inert solvent at a temperature between about −80° and 0° C. The exomethylene double bond reacts with ozone to form in situ an intermediate ozonide which is decomposed, as hereinafter described, to form the 3-hydroxy-3-cephem ester of the formula V.

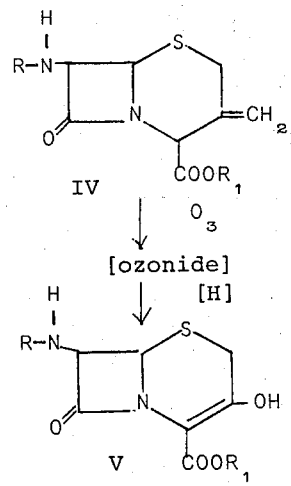

In the above formulae, R is hydrogen or an acyl group derived from a carboxylic acid and which acyl group is non-oxidizable under the described ozonolysis conditions. $R_1$ is an ester forming group and preferably one which is easily removed under hydrogenolysis, or acid or base hydrolysis conditions.

Although the 3-exomethylene cephalosporins can also undergo oxidation with ozone to form the sulfoxide, under the described ozonization conditions the exo double bond reacts preferentially with ozone to form the ozonide. The formation of the sulfoxide occurs as a result of over oxidation. Whereas the exo double bond reacts rapidly with ozone, the reaction at the sulfur atom of the dihydrothiazine ring to form the sulfoxide occurs at a much slower rate. However, the following over oxidation products can be formed in the ozonolysis reaction.

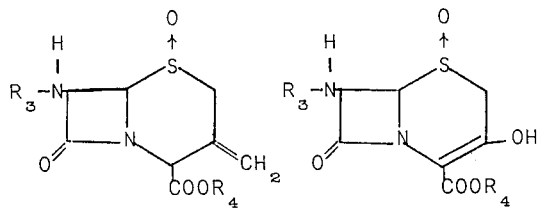

Ozone gas is prepared by means of an ozone generator of the type commonly used in synthetic and analytical chemical work to produce ozone by the action of an electric discharge on oxygen. One such ozone generator is that manufactured by the Welsback Corporation. The ozone is generated in a stream of oxygen which is then passed directly into the reaction vessel. The percentage of ozone contained in the oxygen stream can be varied as desired, for example, by varying the rate of flow of oxygen through the ozonizer as well as by varying the intensity of the electric discharge. The percentage of ozone in the oxygen stream can be determined iodometrically by titrating with sodium thiosulfate the amount of iodine liberated from a standard solution of potassium iodide by ozone from the generator. The percentage of ozone in the oxygen stream is not critical, however for convenience in carrying out the ozonolysis method of this invention an estimate of the amount of ozone flowing into the reaction mixture enables one to determine the time at which the desired reaction should be complete and thus minimizes the formation of over oxidation products.

Alternatively, the ozonolysis reaction can be followed chromatographically. For instance, a small aliquot of the reaction mixture is withdrawn, the ozonide decomposed, and the amount of unreacted starting material and 3-hydroxy-3-cephem product present in the sample is assessed by a comparison of the thin layer chromatogram with that of a known amount of starting material and 3-hydroxy-3-cephem compound.

Inert solvents which can be used in the ozonolysis are those solvents in which the 3-exomethylene cepham esters are at least partially soluble and which are unreactive with ozone under the described conditions. Commonly used organic solvents such as methanol, ethanol, ethyl acetate, methyl acetate, and methylene chloride are satisfactory.

The concentration of the starting material in the inert solvent is not critical and it is preferred to use a solvent volume sufficient to form a complete solution.

The preferred temperature in the ozonolysis reaction is between about −80° and −50° C.

When ozonide formation is complete as determined by either method described above, any excess ozone present in the reaction mixture is purged from the mixture by bubbling nitrogen or oxygen through the mixture.

Following the removal of any excess ozone, the ozonide is decomposed by adding to the reaction mixture a mild reducing reagent selected from the group consisting of sodium bisulfite, sulfur dioxide, and trimethyl phosphite to provide the 3-hydroxy-3-cephem-4-carboxylic acid ester. The decomposition is carried out by adding an excess of the reducing agent and then stirring the reaction mixture at a temperature of about −80° to 0° C. until the reaction mixture is negative in the potassium iodide-starch test.

A preferred reagent for decomposing the intermediate ozonide is gaseous sulfur dioxide. This reagent is preferred since it is completely volatilized from the reaction mixture during the subsequent work-up and thus does not complicate the recovery of the reaction product.

The 7-acylamido-3-hydroxy-3-cephem-4-carboxylic acid esters are recovered from the reaction mixture by first evaporating the mixture to dryness and thereafter extracting the product from the residue. Alternatively, N-acylated 3-hydroxy-3-cephem esters can be recovered from the organic liquid phase of the decomposition mixture by separating the liquid phase from insolubles, and after washing and drying, the organic layer is evaporated to yield the 3-hydroxy ester.

The 3-hydroxy nucleus ester, a 7-amino-3-hydroxy-3-cephem-4-carboxylic acid ester, is best isolated in the form of a salt as for example, the hydrochloride or hydrobromide salt.

When an ester of 7-amino-3-exomethylenecepham-4-carboxylic acid (Formula IV, R=H) is ozonized it is preferable to use a salt of this nucleus, for example, the hydrochloride or p-toluenesulfonate salt.

In a specific example of the preparation of a 3-hydroxy-3-cephem ester, p-methoxybenzyl 7-phenoxyacetamido-3-exomethylenecepham-4-carboxylate is dissolved in ethyl acetate and is reacted with ozone at a temperature of about −78° C. The excess ozone is expelled by bubbling oxygen through the cold solution. The ozonide is decomposed by adding excess sodium bisulfite to the reaction mixture at 0° C. with stirring. The organic layer is decanted from the insolubles and is washed, dried and evaporated to yield p-methoxybenzyl 7-phenoxyacetamido-3-hydroxy-3-cephem-4-carboxylate.

In a further example, p-nitrobenzyl 7-amino-3-methylenecepham-4-carboxylate hydrochloride is dissolved in methanol and ozone is bubbled through the solution at a temperature of about −78° C. Excess ozone is purged from the mixture with nitrogen and the ozonide is decomposed by bubbling sulfur dioxide through the mixture. The reaction mixture is evaporated to dryness and the residue, p-nitrobenzyl 7-amino-3-hydroxy-3-cephem-4-carboxylate is obtained as the hydrochloride salt.

The 3-halo-3-cephem starting materials are prepared either by the direct halogenation of a 7-acylamido-3-hydroxy-3-cephem-4-carboxylic acid ester or by the acylation of a 7-amino-3-halo-3-cephem-4-carboxylic acid or ester thereof (formula V, R=H). The 7-amino-3-halo-3-cephem-4-carboxylic acid or ester is prepared either by the direct halogenation of the corresponding 7-amino-3-hydroxy ester or by the cleavage of the 7-acyamido side chain of a 7-acylamido-3-halo cephem ester.

The 3-chloro or bromo-3-cephem esters are prepared by reacting a 7-acylamido 3-hydroxy-3-cephem ester or a 3-hydroxy-3-cephem nucleus ester in dimethylformamide (DMF) with a reactive chloro or bromo compound which forms with DMF the chloro or bromo dimethyliminium chloride or bromide as represented by the formula

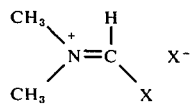

wherein X and X⁻ represent chloro or bromo and chloride or bromide, respectively. The reactive halo iminium halide of the above formula is formed in situ and is a highly reactive chlorinating or brominating intermediate. Chloro and bromo compounds which form the above iminium halide include the commonly used chlorinating agents such as phosgene (carbonyl chloride), oxalyl chloride, thionyl chloride, and the phosphorus chlorides, for example, phosphorus trichloride and phosphorus oxychloride (phosphoryl chloride). Brominating reagents which can be employed in the present invention include carbonyl dibromide, oxalyl bromide, thionyl bromide (sulfurous oxybromide), and the phosphorus bromides, phosphorus oxybromide, and phosphorus tribromide. Phosphorus pentachloride can be employed in the preparation of the 3-chloro-3-cephem compounds of the invention, however this reagent concurrently reacts with the 7-acylamido side chain of the starting material to form the imino chloride, the reactive intermediate in the well known cephalosporin side chain cleavage reaction. Accordingly, it is preferable to use one of the other named chlorinating agents.

The chlorination and bromination of a 3-hydroxy cephem ester is conveniently carried out by employing dry DMF as the solvent. The DMF is preferably dried over a molecular sieve before use. A co-solvent can be employed along with excess DMF although such is not required. For example, a co-solvent such as tetrahydrofuran, dioxane, methylene chloride, dimethylacetamide or dimethyl sulfoxide can be used along with DMF. The brominating or chlorinating agent such as one of those enumerated above is desirably used in an amount corresponding to two equivalents of the amount of 3-hydroxy cephem ester starting material used. The reaction is carried out by adding the halogenating reagent to a solution of the 3-hydroxy-cephem ester in dry DMF maintained at a temperature of about 5° to 15° C. and allowing the reaction mixture to stand at room temperature for between 4 and 8 hours or longer. The reaction is initially exothermic and accordingly the reaction vessel is maintained in an ice-water bath to maintain the temperature below about 25° C. during the initial phase of the reaction. Thereafter the reaction mixture is allowed to stand at or about room temperature for the duration of the reaction. The extent to which the reaction has proceeded can be determined by thin layer chromatography.

Alternatively, the chlorination and bromination can be carried out by first preparing a mixture of the halogenating reagent in DMF to perform the haloiminium halide, and then adding the mixture to a solution of the 3-hydroxy-3-cephem ester in DMF.

The 3-chloro- or 3-bromo-3-cephem esters are recovered from the reaction product mixture by pouring the mixture into a water-ethyl acetate mixture and separating the organic phase containing the product. The organic phase is washed, dried and is evaporated to afford the 3-halo-3-cephem ester as an amorphous residue. The product is obtained crystalline in many instances by trituration of the residue with ether or with n-hexane.

The preferred chlorinating and brominating reagents are phorphorus trichloride and phosphorus tribromide.

The 7-amino-3-halo-3-cephem-4-carboxylic acids are preferably obtained by the cleavage of the 7-acyl group of a 7-acylamido-3-halo-3-cephem-4-carboxylic acid ester followed by removal of the carboxylic acid protecting ester group.

Representative of the preferred starting materials the 3-chloro-3-cephem esters are p-nitrobenzyl 7-[2-(2-thienyl)acetamido]-3-chloro-3-cephem-4-carboxylate, p-methoxybenzyl 7-phenoxyacetamido-3-chloro-3-cephem-4-carboxylate, p-nitrobenzyl 7-D-mandelamido-3-chloro-3-cephem-4-carboxylate, diphenylmethyl 7-benzamido-3-chloro-3-cephem-4-carboxylate, 2,2,2-trichloroethyl 7-acetamido-3-chloro-3-cephem-4-carboxylate, p-nitrobenzyl 7-(α-carboxyphenylacetamido)-3-chloro-3-cephem-4-carboxylate, p-nitrobenzyl 7-(D-phenylglycylamido)-3-chloro-3-cephem-4-carboxylate wherein the amino group is protected with the t-butyloxycarbonyl group.

The 3-sulfonyloxy-3-cephem esters are prepared with the 3-hydroxy-3-cephem esters by reacting a 7-acylamido-3-hydroxy-3-cephem-4-carboxylic acid ester with a $C_1$–$C_6$ alkylsulfonyl halide, a phenylsulfonyl halide, or a substituted phenylsulfonyl halide at a temperature between about −5° and 35° C. in an aprotic solvent in the presence of a hydrogen halide acceptor. 7-Acylamido-3-hydroxy-3-cephem-4-carboxylic acid esters which can be used in the preparation are represented by the following formula

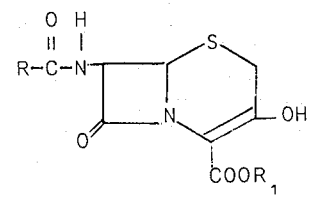

wherein R and $R_1$ have the same meanings as defined for formula I.

Representative of the alkyl and phenysulfonyl halides which can be used are methanesulfonyl chloride, methanesulfonyl bromide, ethanesulfonyl chloride, n-butanesulfonyl chloride, n-hexanesulfonyl bromide, phenylsulfonyl chloride, p-chloro-phenylsulfonyl chloride, p-fluorophenylsulfonyl chloride, p-toluenesulfonyl chloride, p-toluenesulfonyl bromide, 3- or 4-nitrobenzenesulfonyl chloride or bromide, 3-ethylbenzensulfonyl chloride and 3-bromobenzenesulfonyl chloride or bromide.

Aprotic solvents which can be employed are the ether solvents such as tetrahydrofuran, dioxane and the dimethyl ether of ethylene glycol or like ether solvents. A preferred solvent which can be used is dimethylacetamide.

The reaction is carried out in the presence of a hydrogen halide acceptor such as an unreactive tertiary amine such as triethylamine or pyridine or an alkylene oxide, for example, propylene or butylene oxide. The preferred hydrogen halide acceptor is propylene oxide. The tertiary amine type acceptors tend to cause isomerization of the 3-cephem to a 2-cephem compound. With an alkylene oxide such isomerization is kept to a minimum with most sulfonyl halides.

The reaction is carried out by the addition of the stoichiometric amount of the sulfonyl halide, or a slight excess thereof, to a solution of the 3-hydroxy-3-cephem ester in the aprotic solvent containing at least a stoichiometric amount of the hydrogen halide acceptor. The reaction mixture is stirred and preferably between about 10° and 25°C. for between 3 and 12 hours. The sulfonate ester product is recovered from the reaction mixture by extraction with an organic solvent such as ethyl acetate or methylene chloride and is recovered from the extract. The 3-sulfonate esters can be purified by chromatography over silica gel.

When the starting material contains a functional group in the 7-acylamido side chain which is capable of reacting with the sulfonyl halide, the reactive group is protected with a suitable protecting group. For example, the α-amino group of the phenylglycyl side chain can be protected during the sulfonyl ester formation with a variety of amino protecting groups. For example, the urethan protecting groups such as t-butyloxycarbonyl, 2,2,2-trichloroethoxycarbonyl, benzyloxycarbonyl, p-nitrobenzyloxycarbonyl, and the like; the enamine protecting groups formed with ethyl acetoacetate, acetyl acetone, and the like; the trityl group and other amino protecting groups. An amino substituent of a phenyl group in the 7 side chain can also be protected with the same groups. Likewise, an hydroxy group located in the 7-acylamido side chain, for example, in the mandeloyl side chain, is protected with a readily removable group such as, for example, the formyl group and the trichloroethoxycarbonyl group. Following the sulfonylation reaction such protecting groups are removed. Also, the C₄ carboxylic acid protecting group is removed to provide 3-sulfonyloxy-3-cephem-4-carboxylic acid antibiotic compound.

The foregoing description of the preparation of the sulfonate esters is illustrated in the following reaction scheme.

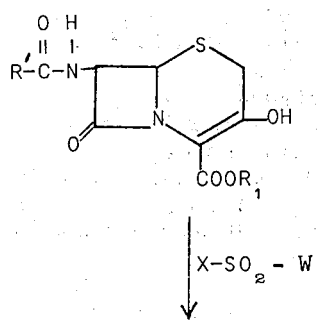

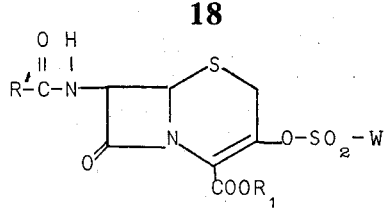

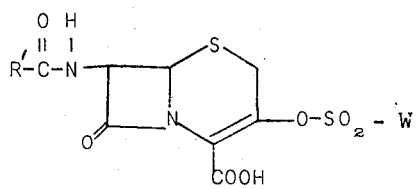

wherein R¹, R₁, W have the same meanings as previously defined.

In a specific example, p-nitrobenzyl 7-(N-t-butyloxycarbonyl-D-phenylglycylamido)-3-hydroxy-3-cephem-4-carboxylate is reacted with methanesulfonyl chloride in dimethylacetamide in the presence of propylene oxide at about 5° C. to yield 7(N-t-butyloxycarbonyl D-phenylglycylamido)-3-methylsulfonyloxy-3-cephem-4-carboxylic acid p-nitrobenzyl ester. The product is hydrogenated over pre-reduced palladium on carbon catalyst in an inert solvent to effect removal of the p-nitrobenzyl ester group and the de-esterified product is then reacted with p-toluenesulfonic acid in acetonitrile to effect the removal of the t-butyloxycarbonyl group and provide the antibiotic 7-(D-phenylglycylamido)-3-methylsulfonyloxy-3-cephem-4-carboxylic acid.

Antibiotic Properties of 3-thio Substituted 3-cephem Carboxylic Acids

The cephalosporin compounds of this invention (formula I, wherein R₁ = H) and the pharmaceutically acceptable nontoxic salts thereof are useful antibacterial compounds which inhibit the growth of microorganisms pathogenic to animals and man.

In the tables which follow, the in vitro antibacterial activity for representative compounds of the invention is presented.

In Table I, the antibacterial activity of 7-(D-phenylglycylamido)-3-(1-methyl-1H-tetrazole-5-ylthio)-3-cephem-4-carboxylic acid against 6 bacterial isolates is shown. The activity was determined in the standard Disc-plate test. The antibiotic was dissolved in pH 6 phosphate buffer and the solution diluted with pH 6 phosphate buffer to concentrations of 100, 50, 25 and 12.5 μg/ml. Paper discs were saturated with each solution of the antibiotic and were placed on nutrient agar plates seeded with approximately 10⁵ bacteria per ml. of nutrient agar. The plates were then incubated and the clear zones of growth inhibition surrounding the discs were measured.

Table I

Antibacterial Activity of
7-(D-Phenylglycylamido)-3-
(1-methyl-1H-tetrazole-5-ylthio)-
3-cephem-4-carboxylic Acid

| Bacterial Isolate | Zone Diameters (mm) Antibiotic Concentration ($\mu$g) | | | |
|---|---|---|---|---|
| | 100 | 50 | 25 | 12.5* |
| Salmonella typhosa SA12 | 20.8 | 17.2 | 16.0 | 14.0 |
| Escherichia coli EC14 | 19.4 | 16.7 | 15.6 | 13.6 |
| Proteus mirabilis PR6 | 18.2 | 15.2 | 14.0 | 11.6 |
| Staphylococcus aureus 3055 | 22.0 | 18.0 | 15.0 | <6 |
| Sarcina lutea X186 | 35.5 | 32.0 | 30.5 | 27.0 |
| Bacillus subtilis X12 | 25.0 | 23.0 | 19.0 | 6.5 |

*Lowest concentration tested.

Table II

Antibacterial Activity of
7-[2-(2-Thienyl)acetamido]-3-(1-methyl-1H-tetrazole-5-ylthio)-
3-cephem-4-carboxylic Acid
Disc-Plate Method

| Test Microorganism | Zone Diameters (mm) Antibiotic Concentration 0.1 mg/ml |
|---|---|
| Staphylococcus aureus 3055 | 32 |
| Bacillus subtilis | 22 |
| Sarcina lutea | 30 |
| Proteus vulgarus | 17 |
| Salmonella gallinarum | t* |
| Escherichia coli | 17 |
| Bacillus subtilis | 37 |
| Escherichia coli | 21 |

*t=trace zone of inhibition.
**test run on minimal medium.

The minimum inhibitory concentration (MIC) of 7-[2-(2-thienyl)acetamido]-3-(1-methyl-1H-tetrazole-5-ylthio)-3-cephem-4-carboxylic acid against gram-negative organisms and penicillin resistant isolates of Staphylococcus is shown in the following Table III. The MIC values were obtained in the Gradient-Plate test method (Bryson and Szybalski, *Science*, 116, 45–46 (1952).

Table III

Antibacterial Activity
vs.
Gram-Negative and Penicillin Resistant Organisms of
7-[2-(2-Thienyl)acetamido]-3-
(1-methyl-1H-tetrazole-5-ylthio)-
3-cephem-4-carboxylic acid

| Test Microorganisms | Minimum Inhibitory Concentration $\mu$g/ml |
|---|---|
| Shigella sp. | 16 |
| Escherichia coli | 16 |
| Klebsiella pneumoniae | 16 |
| Aerobacter aerogenes | 7.5 |
| Salmonella heidelberg | 4.0 |
| V41* | >20 |
| V32* | >20 |
| V84* | > 0.1 |
| X1.1* | > 0.1 |

*Clinical isolates of penicillin resistant S. aureus.

The antibacterial activity of the cephalosporin compounds of the invention wherein $R_2$ is $C_1$-$C_4$ alkyl, phenyl, or substituted phenyl, is somewhat less than the activity displayed by the preferred compounds of this invention wherein $R_2$ is one of the described heterocyclic groups. The activity of the cephalosporin compounds wherein $R_2$ is $C_1$-$C_4$ alkyl, phenyl, or substituted phenyl, is illustrated by the minimum inhibitory concentration against gram-negative organisms displayed by 7-[2-(2-thienylacetamido]-3-methylthio-3-cephem-4-carboxylic acid in the gradient plate test. In this test, this compound demonstrated minimum inhibitory concentrations against *Klebsiella pneumoniae*, *Aerobacter aerogenes*, and *Salmonella heidelberg* of 14, 21.5, and 25 mcg./ml., respectively.

The antibiotic compounds of this invention are useful for controlling the growth of pathogenic microorganisms and in combating infectious diseases when administered parenterally. They may also be used for maintaining physiological fluids free of bacterial contamination.

The antibiotics of this invention are acidic compounds and, accordingly, react with inorganic and organic bases to form salts. In general, these salts also possess antibacterial activity and can be used as more soluble forms of the antibiotics. Salts formed with inorganic bases such as the alkali metal carbonates, for example the lithium, sodium, and potassium carbonates or bicarbonates can be prepared with the free acid form of the antibiotic by methods employed for the preparation of salts of other cephalosporin antibiotic acids. Likewise, the antibiotics of this invention can form salts with the organic amines of which may be mentioned secondary amines such as diethylamine, diisopropylamine, dicyclohexylamine, and dibenzylamine. Also, the ethanolamines, such as monoethanolamine and diethanolamine can also be used to form salts of the cephalosporin acids.

The following examples further illustrate the compounds described herein as well as their method of preparation.

A. Preparation of 3-hydroxy and 3-halo-3-cephem Starting Materials.

EXAMPLE 1 p-Nitrobenzyl
7-amino-3-methylenecepham-4-carboxylate
hydrochloride.

To a solution of 965 mg. (2 mmole) of p-nitrobenzyl 7-phenoxyacetamido-3-methylenecepham-4-carboxylate in 10 ml. of methylene chloride were added 175 mg. of dry pyridine and 460 mg. of phosphorus pentachloride and the mixture was stirred at room temperature for 6 hours. One ml. of isobutanol was added to the mixture which was then stored at 0° C. overnight. The rection product, p-nitrobenzyl 7-amino-3-methylenecepham-4-carboxylate hydrochloride, which formed as a crystalline precipitate was filtered to yield 430 mg. (58% yield).

Elemental Analysis for $C_{15}H_{16}N_3O_5SCl$: Theory: C, 46.69; H, 4.18; N, 10.89; Found: C, 46.40; H, 4.20; N, 10.62.

I.R. (Nujol Mull)
 Carbonyl absorption at 5.65 ($\beta$-lactam) and 5.75 (ester) microns.

N.M.R. (DMSO $d_6$) signals at 6.34 (2d, 2H, $C_2$—$H_2$), 4.98 (d, 1H, $C_6$—H); 4.7–4.4 (m, 6H, $C_4$—H, ester $CH_2$, $C_4$—$CH_2$ and $C_7$—H); and 2.4–1.6 (m, 4H, aromatic H) tau.
 4.7–4.55 (m, 4H, $C_4$—H, $C_3$—$CH_2$ and $C_7$—H)
 3.2–2.0 (m, 8H, aromatic H) tau.

EXAMPLE 2 p-Nitrobenzyl
7-amino-3-hydroxy-3-cephem-4-carboxylate
hydrochloride.

A solution of 3.85 g. of p-nitrobenzyl 7-amino-3-methylenecepham-4-carboxylate hydrochloride, prepared as described by Example 1, in 600 ml. of methanol was cooled in an acetone-dry ice bath. Ozone was bubbled through the reaction mixture for approximately 20 minutes at which time the reaction mixture developed a faint blue coloration. Nitrogen was then passed through the reaction mixture to expel excess ozone. Next, the intermediate ozonide was decomposed by passing sulfur dioxide gas through the reaction mixture until the mixture gave a negative potassium iodide-starch test.

The reaction mixture was evaporated in vacuo and the residue was dissolved in 200 ml. of 0.1N hydrogen chloride in methylene chloride. The solution was evaporated to dryness and the residual reaction product was dissolved in acetone. On cooling, 3.15 g. of p-nitrobenzyl 7-amino-3-hydroxy-3-cephem-4-carboxylate hydrochloride precipitated as a crystalline solid.

I.R. (Nujol Mull):
  Carbonyl absorption at
    5.55 ($_\beta$-lactam carbonyl) and
    5.02 (ester carbonyl hydrogen bonded to 3 hydroxy) microns.
Electrometric titration (66% DMF) pKa 4.0 and 6.3

EXAMPLE 3 p-Nitrobenzyl
7-[2-(2-thienyl)acetamido]-3-hydroxy-3-cephem-4-carboxylate.

To a solution of 1.55 g. of p-nitrobenzyl 7-amino-3-hydroxy-3-cephem-4-carboxylate hydrochloride in 30 ml. of acetone containing 364 mg. (0.5 ml., 3.6 mmole) of triethylamine was added 962 mg. of urea. With stirring at room temperature, a solution of 730 mg. (4.4 mmole) of 2-thiophene acetyl chloride in 20 ml. of acetone was added dropwise to the mixture. After 2.5 hours the reaction mixture was filtered and evaporated. The residue was dissolved in ethyl acetate and the solution was washed successively with water, a 5% solution of sodium bicarbonate, 5% hydrochloric acid, and a saturated solution of sodium chloride. The washed solution was dried and then was concentrated by evaporation in vacuo to yield 1.2 g. of the reaction product as a crystalline residue. The product was recrystallized from ethyl acetate to yield pure p-nitrobenzyl 7-[2-(2-thienyl)acetamido]-3-hydroxy-3-cephem-4-carboxylate having the following spectral properties.

I.R. (Nujol Mull): absorption peaks at 3.0 (amide NH), 5.68 ($\beta$-lactam carbonyl), and 6.1 (amide, and ester hydrogen bonded to 3 OH) microns.

N.M.R. (CDCl$_3$/DMSO d$_6$): signals at 6.54 (2d, 2H, C$_2$H$_2$), 6.16 (s, 2H, side-chain CH$_2$), 4.90 (d, 1H, C$_6$H) 4.60 (d, 2H, ester CH$_2$), 4.43 (q, 1H, C$_7$H), 3.1–1.6 (m, 7H, aromatic H) and 1.30 (d, 1H, amide NH) tau.

EXAMPLE 4 p-Nitrobenzyl
7-pheylacetamido-3-hydroxy-3-cephem-4-carboxylate

Following the oxonization procedures described in Example 2, a solution of 350 mg. of p-nitrobenzyl 7-phenylacetamido-3-methylenecepham-4-carboxylate in 250 ml. of methylene chloride was cooled to −78° C. and was ozonized. The intermediate ozonide was decomposed in situ with sulfur dioxide and the reaction product was recovered and obtained crystalline by extraction with ethyl acetate.

Elemental analysis for C$_{22}$H$_{19}$N$_3$O$_7$S: Theory: C, 56.28; H, 4.80; N, 8.95; Found: C, 56.11; H, 4.15; N, 8.74.

N.M.R. (CDCl$_3$): signals at 6.68 (2d, 2H, C$_2$H$_2$), 6.37 (s, 2H, side-chain CH$_2$), 5.03 (d, 1H, C$_6$H), 6.66 (d, 2H, ester CH$_2$), 4.40 (q, 1H, C$_7$H), 2.7 (m, 6H, amide NH and aromatic H), 2.53–1.70 (q. 4H, aromatic H) and a singlet in low field integrating for 1H of C$_3$ hydroxyl group tau.

I.R. (Nujol Mull): absorption peaks at 3.04 (amide), 5.60 and 6.0 ($\beta$-lactam, ester and amide carbonyls) microns.

EXAMPLE 5 p-Nitrobenzyl
7-(D-$\alpha$-phenyl-$\alpha$-formyloxyacetamido)-3-hydroxy-3-cephem-4-carboxylate.

To a solution of 1.54 g. of p-nitrobenzyl 7-amino-3-hydroxy-3-cephem-4-carboxylate hydrochloride in 120 ml. of acetone and 40 ml. of water was added 936 mg. of sodium bisulfite. With stirring a solution of 960 mg. of O-formyl-D-mandelic acid chloride in 20 ml. of anhydrous acetone was added dropwise at room temperature. The reaction mixture was stirred at room temperature for 16 hours and was then evaporated to remove acetone. The aqueous residue was slurried with ethyl acetate and the organic layer separated. The extract was washed with water was dried and evaporated. The crystalline residue was triturated with diethyl ether and dried to yield 1 g. of p-nitrobenzyl 7-(D-$\alpha$-phenyl-$\alpha$-formyloxyacetamido)-3-hydroxy-3-cephem-4-carboxylate.

Elemental analysis for C$_{23}$H$_{19}$N$_3$O$_9$S: Theory: C, 53.80; H, 3.73; N, 8.18; Found: C, 53.51; H, 3.81; N, 8.46

I.R. (CHCl$_3$): carbonyl absorption peaks at 5.55, 5.73, 5.85 and 5.93 microns.

N.M.R. (CDCl$_3$): signals at 6.61 (s, 2H, C$_2$H$_2$), 4.95 (d, 1H, C$_6$H), 4.61 (d, 2H, ester CH$_2$), 4.39 (q, 1H, C$_7$H), 3.70 (s, 1H, $\alpha$-CH), and 2.80–1.70 (m, 11H, amide NH and aromatic H) tau.

EXAMPLE 6

Diphenylmethyl
7-[2-(2-thienyl)acetamido]-3-chloro-3-cephem-4-carboxylate.

a. To a solution of 34 g. (100 mmole) of 7-[2-(2-thienyl)acetamido]-3-methylenecepham-4-carboxylic acid in 500 ml. of methylene chloride was added 21.4 g. (110 mmole) of diphenyl diazomethane and the resulting mixture was stirred for 2 hours at room temperature. The solvent was evaporated under reduced pressure and the residue was dissolved in ethyl acetate. The ethyl acetate solution was washed with a 5% solution of sodium bicarbonate, then with water and was dried over magnesium sulfate. The dried solution was concentrated to a small volume. On standing 40 g. of diphenylmethyl 7-[2-(2-thienyl)acetamido]-3-methylenecepham-4-carboxylate melting at about 132°–133° C. precipitated as a crystalline solid.

I.R. (chloroform): absorption peaks at 2.9 (amide N—H), 5.65, 5.75, and 5.93 ($\beta$-lactam, ester and amide carbonyls respectively) and 6.62 (amide II) microns N.M.R. (CDCl$_3$): signals at 6.72 (ABq, 2H, C$_2$—H$_2$), 6.21 (s, 2H, $\alpha$-CH$_2$), 4.83–4.65 (m, 4H, C$_4$—H, C$_6$—H and C$_3$—CH$_2$), 4.39 (q, 1H, C$_7$—H), 3.4–2.65 (m, 15H, C$_7$-NH, ester CH and aromatic H) tau.

b. To the solution of 8.1 g. (16 mmole) of the above ester in 80 ml. of methylene chloride were added 1.57 g. (1.6 ml., 19.6 mmole) of dry pyridine and 3.8 g. (8.1 mmole) of phosphorus pentachloride. The reaction mixture was stirred for 2 hours at room temperature and was thereafter cooled in an ice-water bath. The cold mixture was treated with 8 ml. of isobutanol with stirring. Stirring was continued for 2 hours during which time 3 g. of diphenylmethyl 7-amino-3-methylenecepham-4-carboxylate hydrochloride formed as a crystalline precipitate. The product was filtered and washed with methylene chloride and vacuum dried.

Elemental analysis (percent) for C$_{21}$H$_{21}$N$_2$O$_3$SCl: Theory: C, 60.50; H, 5.08; N, 6.72; Cl, 8.50; Found: C, 60.70; H, 5.02; N, 6.71; Cl, 8.80.

NMR (DMSO d$_6$): signals at 6.45 (ABq, 2H, C$_2$—H$_2$), 5.00 (d, 1H, C$_6$—H), 4.68 (d, 1H, C$_7$—H), 4.60 (s, 2H, 3—CH—2), 4.44 (s, 1H, C$_4$-H), 3.10 (s, 1H, ester CH), and 2.61 (s, 10H, aromatic H) tau.

c. The 7-amino-3-exomethylenecepham ester hydrochloride salt product, 2.1 g. (5 mmole) was dissolved in 200 ml. of methanol and the solution was cooled in an acetone-dry ice bath. Ozone was bubbled into the cold solution for 7 minutes to form the intermediate ozonide. The ozonide was decomposed by passing a stream of sulfur dioxide gas through the reaction mixture for 2 minutes. Thereafter the reaction mixture was evaporated and the residue was triturated with diethyl ether to yield 1.6 g. of diphenylmethyl 7-amino-3-hydroxy-3-cephem-4-carboxylate hydrochloride as a crystalline solid.

N.M.R. (CDCl$_3$): signals at 6.4 (ABq, 2H, C$_2$-H$_2$), 5.0–4.5 (m, 2H, C$_6$—H and C$_7$—H), 3.2–2.4 (m, 11H, ester CH and aromatic H) tau.

I.R. (chloroform): carbonyl absorption peaks at 5.57 and 5.70 ($\beta$-lactam and ester carbonyl, respectively) microns.

U.V. (pH 7 buffer): $\lambda$ max 275 m$\mu$, $\epsilon$=7550.

Electrometric titration (60% aq. DMF): titratable groups at 4.5 and 6.5.

d. To a solution of 840 mg. of diphenylmethyl 7-amino-3-hydroxy-3-cephem-4-carboxylate in 10 ml. of water and 10 ml. of acetone was added one gram of sodium bisulfite. The mixture was stirred and 800 mg. of thiophene-2-acetyl chloride in 10 ml. of acetone were added dropwise. The mixture was stirred for 4.5 hours at room temperature and was then evaporated under reduced pressure. The residue was dissolved in a mixture of ethyl acetate and an aqueous 5% solution of sodium bicarbonate. The ethyl acetate layer was separated, washed with water and dried. The dried solution was evaporated and the residue triturated with ether to yield 500 mg. of diphenylmethyl 7-[2-(2-thienyl)acetamido]-3-hydroxy-3-cephem-4-carboxylate.

N.M.R. (CDCl$_3$): signals at 6.79 (s, 2H, C$_2$—H$_2$), 6.16 (s, 2H, $\alpha$-CH$_2$), 5.0 (d, 1H, C$_6$—H), 4.32 (q, 1H, C$_7$—H), 3.05–2.46 (m, 15H, C$_7$—NH, ester CH and aromatic H) tau.

I.R. (chloroform): absorption peaks at 2.9 (amide NH), 5.6, 5.73 and 5.95 ($\beta$-lactam, ester and amide carbonyls, respectively) and 6.65 (amide II) microns.

e. To a solution of 4.2 g. of diphenylmethyl 7-[2-(2-thienyl)acetamido]-3-hydroxy-3-cephem-4-carboxylate in 44 ml. of dry dimethylformamide was added 865 mg. of phosphorus trichloride. The mixture was stirred for 1.5 hours at room temperature and was poured into an ethyl acetate 5% aqueous hydrochloric acid mixture. The ethyl acetate layer was evaporated, was washed with 5% hydrochloric acid, water and was dried. The dried solution was concentrated in vacuo and the product crystallized. The 3-chloro ester was filtered, washed with cold ethyl acetate and dried to yield 2.2 g.

Elemental analysis (percent) for C$_{26}$H$_{21}$N$_2$O$_4$S$_2$Cl: Theory: C, 59.48; H, 4.03; N, 5.34; Cl, 6.75; Found: C, 59.77; H, 4.25; N, 5.40; Cl, 6.91.

N.M.R. (CDCl$_3$): signals at 6.49 (ABq, 2H, C$_2$—H$_2$), 6.22 (s, 2H, $\alpha$-CH$_2$), 5.08 (d, 1H, C$_6$—H), 4.19 (q, 1H, C$_7$—H), 3.13–2.5 (m, 15H, C$_7$—NH, ester CH, and aromatic H) tau.

I.R. (CHCl$_3$): absorption peaks at 2.9 (amide NH), 5.55, 5.72 and 5.90 ($\beta$-lactam, ester and amide carbonyls) and 6.60 (amide II) microns.

U.V. (dioxane): $\lambda$ max 275 m$\mu$, $\epsilon$=8700.

EXAMPLE 7 p-Nitrobenzyl 7-[2-(2-thienyl)acetamido]-3-chloro-3-cephem-4-carboxylate (via thionyl chloride).

To a solution of 1.9 g. (4 mmole) of p-nitrobenzyl 7-[2-(2-thienyl)acetamido]-3-hydroxy-3-cephem-4-carboxylate in 10 ml. of DMF (dried over a molecular sieve) was added 950 mg. (0.58 ml., 8 mmole) of freshly distilled thionyl chloride. The mixture was stirred at room temperature for 6.5 hours and was then poured into 100 ml. of ethyl acetate. The mixture was extracted three times with 30 ml. portions of 5% hydrochloric acid and with a saturated solution of sodium chloride. The washed ethyl acetate solution was filtered and evaporated to dryness in vacuo. The residue was triturated with ether to yield 1.2 g. of p-nitrobenzyl 7-[2-(2-thienyl)acetamido]-3-chloro-3-cephem-4-carboxylate as a brown cyrstalline solid melting at about 164°–166° C.

Elemental analysis (percent) for C$_{20}$H$_{16}$N$_3$O$_6$S$_2$Cl: Theory: C, 48.63; H, 3.27; N, 8.51; Cl, 7.18; Found: C, 48.47; H, 3.29; N, 8.78; Cl, 6.96.

I.R. (Chloroform) showed absorption bands at 2.9 (amide NH), 5.59 ($\beta$-lactam carbonyl), 5.75 (ester carbonyl) and 5.92 microns (amide carbonyl).

U.V. absorption spectrum (acetonitrile) showed maxima at
$\lambda$ max 235 m$\mu$, $\epsilon$ = 12,100 and
$\lambda$ max 268 m$\mu$, $\epsilon$ = 15,800.

The mass spectrum of the product showed a molecular ion of 493 m/e.

N.M.R. (CDCl$_3$) showed signals at 6.39 (ABq, 2H, C$_2$—H$_2$), 6.17 (s, 2H, $\alpha$-CH$_2$), 4.99 (d, 1H, C$_6$—H), 4.64 (s, 2H, ester CH$_2$), 4.19 (q, 1H, C$_7$—H), 3.45 (d, 1H, C$_7$—NH), 3.1–1.67 (m, 7H, aromatic H) tau.

EXAMPLE 8

7-[2-(2-Thienyl)acetamido]-3-bromo-3-cephem-4-carboxylic acid.

To a solution of 19 g. (40 mmole) of p-nitrobenzyl 7-[2-(2-thienyl)acetamido]-3-hydroxy-3-cephem-4-carboxylate in 300 ml. of dry DMF was added 15 g. (56 mmole) of phosphorus tribromide and the reaction mixture was stirred at room temperature overnight. The reaction mixture was poured into a mixture of ethyl acetate and water and the organic phase was separated and washed repeatedly with water and dried over magnesium sulfate. The dried organic phase was evaporated in vacuo to dryness. The crude reaction product residue weighing about 9 g. was purified by chromatography over 500 g. of silica gel using ethyl acetate-hexane (55:45 v:v) as eluent. The eluate was evaporated to dryness under reduced pressure and the product, p-nitrobenzyl 7-[2-(2-thienyl)acetamido]-3-bromo-3-cephem-4-carboxylate was obtained crystalline by the triturating the dry residue with diethyl ether.

U.V. (ethanol) λ max, 270 mµ ($\epsilon$=13,300)
and λ max. 243 mµ ($\epsilon$=12,700)

Elemental analysis calculated for $C_{20}H_{16}BrN_3O_6S_2$: Theory: C, 44.61; H, 3.00; N, 7.81; Br, 14.84; Found: C, 44.78; H, 3.03; N, 7.65; Br, 14.91.

Nuclear magnetic resonance spectrum (DMSO d$_6$) showed signals at 6.21 (s, 2H, α-CH$_2$), 5.98 (ABq, 2H, C$_2$—H$_2$), 4.72 (d, 1H, C$_6$—H), 451 (s, 2H, ester-CH$_2$), 420 (q, 1H, C$_7$—H), 3.04–1.74 (m, 7H; aromatic H) and 0.66 (d, 1H, C$_7$—CH) tau.

The above 3-bromo ester was de-esterified in the following manner. The ester, 545 mg. (1.0 mmole) was hydrogenated at room temperature in ethanol in the presence of prereduced 5 percent palladium-on-carbon catalyst. The catalyst was filtered and the filtrate evaporated under reduced pressure to dryness. The residual product was triturated with diethyl ether to yield 180 mg. (44 percent) of crystalline product, 7-[2-(2-thienyl)acetamido]-3-bromo-3-cephem-4-carboxylic acid.

Electrometric titration (66 percent aqueous DMF) showed a pKa of 4.4 and an apparent molecular weight of 393. The calculated molecular weight = 403.

Elemental analysis calculated for $C_{13}H_{11}BrN_2O_4S_2$. One-half diethyl etherate: Theory: C, 49.91; H, 3.66; N, 6.36; Br, 18.15; Found: C, 41.29; H, 3.20; N, 6.29; Br, 18.50.

Nuclear magnetic resonance spectrum (CDCl$_3$) showed signals at 8.8 (t, diethyl ether-CH$_3$), 6.68–5.86 (m, C$_2$—H$_2$, α-CH$_2$ and diethyl ether-CH$_2$), 4.90 (d, 1H, C$_6$—H), 3.0–2.63 (m, 3H, aromatic-H), and 1.9 (d, 1H, amide NH) tau.

EXAMPLE 9

7-(D-Mandelamido)-3-chloro-3-cephem-4-carboxylic acid

To a suspension of 812 mg. (2 mmole) of p-nitrobenzyl 7-amino-3-chloro-3-cephem-4-carboxylic acid hydrochloride in 40 ml. of ethyl acetate was added a solution of 520 mg. (5 mmole) of sodium bisulfite in 40 ml. of water. The mixture was vigorously stirred while 395 mg. (2.2 mmole) of D-mandelic acid O-carboxy anhydride were added. The mixture was stirred for 1.5 hours at room temperature and the aqueous layer was separated from the ethyl acetate layer and washed with ethyl acetate. The ethyl acetate wash was combined with the ethyl acetate layer and the combined wash and ethyl acetate layer was washed several times with water and then dried and evaporated to yield the reaction product as a dry residue. The residue was triturated with ether to yield 685 mg. of p-nitrobenzyl 7-(D-mandelamido)-3-chloro-3-cephem-4-carboxylate melting at about 158°–164° C. with decomposition.

Elemental analysis for $C_{22}H_{18}N_3O_7SCl$: Theory: C, 52.44; H, 3.60; N, 8.34; Cl, 7.04%; Found: C, 52.25; H, 3.45; N, 8.58; Cl, 6.82%.

N.M.R. (CDCl$_3$): signals at 6.24 (ABq, 2H, C$_2$—H$_2$), 5.0–4.7 (m, 2H, C$_6$—H and α-H), 4.57 (s, 2H, ester CH$_2$), 6.23 (q, 1H, C$_7$—H), and 2.8–1.2 (m, 10H, aromatic H and C$_7$—NH) tau.

U.V. (acetonitrile): λ max 265 mµ ($\epsilon$ = 18,600).

The reaction product, 200 mg., was reacted with hydrogen in the presence of 5% palladium on carbon to effect removal of the p-nitrobenzyl ester group and provide 75 mg. of 7-(D-mandelamido)-3-chloro-3-cephem-4-carboxylic acid.

N.M.R. (D$_2$O-sodium bicarbonate): signals at 6.42 (ABq, 2H, C$_2$—H$_2$), 4.90 (d, 1H, C$_6$—H), 4.68 (s, 1H, α-CH), 4.37 (d, 1H, C$_7$—H) and 2.49 (s, 5H, aromatic H) tau.

B. Preparation of Sulfonate Esters

EXAMPLE 10 p-Nitrobenzyl 7-[2-(2-thienyl)acetamido]-3-methylsulfonyloxy-3-cephem-4-carboxylate.

To a solution of 4.75 g. (10 mmole) of p-nitrobenzyl 7-[2-(2-thienyl)acetamido]-3-hydroxy-3-cephem-4-carboxylate in 50 ml. of dry dimethylacetamide were added 2 ml. of propylene oxide. To the solution was added with stirring one equivalent of methanesulfonyl chloride and stirring was continued for 3 hours. The reaction mixture was then taken up in ethyl acetate and the solution was washed with a saturated solution of sodium chloride. The washed organic phase was evaporated in vacuo to dryness to obtain the reaction product mixture as a residue. The reaction product was purified by preparative thin layer chromatography on silica gel using for elution 65 percent ethyl acetate/hexane.

The purified product gave the following percent elemental composition on microanalysis.

Calculated for $C_{21}H_{19}N_3O_9S_3$; Theory: C, 45.56; H, 3.46; N, 7.59; S, 17.38; Found: C, 45.74; H, 3.56; N, 7.30; S, 17.06.

The nuclear magnetic resonance spectrum and the infrared absorption spectrum were in agreement with the structure of the product formed.

N.M.R. (DMSO d$_6$) delta values: 3.47 (s, 3H, methyl); 3.80 (broad s, 2H, side chain CH$_2$); 3.91 (q, 2H, C$_2$H$_2$); 5.29 (d, 1H, C$_6$H); 5.46 (broad s, 2H, ester CH$_2$); 5.84 (q, 1H, C$_7$H); 6.86–7.44 (m, 3H, thiophene); and 7.98 (q, 4H, phenyl).

I.R. (mull) 1785, 1350, and 1158 cm$^{-1}$

U.V. (Ethanol) λ max 264 mµ.

The above product (2 g.) was dissolved in a solvent mixture of 15 ml. of methanol and 20 ml. of tetrahydrofuran and 3 g. of prereduced 5 percent palladium on carbon catalyst were added. (The catalyst had been prereduced in 15 ml. of methanol for 1 hour prior to use.) The mixture was hydrogenated for 1.5 hours during which time the theoretical hydrogen uptake had occurred.

The catalyst was filtered and the filtrate was evaporated to dryness on a rotary evaporator in vacuo. The residue was dissolved in 20 ml. of ethyl acetate and 20 ml. of cold water were added. The pH of the solution was adjusted to pH 7 with a solution of sodium bicarbonate and the organic layer was separated. Ethyl acetate was layered over the aqueous phase and the pH adjusted to 2.0 with 1N hydrochloric acid. The organic layer was separated and combined with an ethyl acetate extract of the acidified aqueous layer. The combined extract and organic layer were dried over magnesium sulfate and evaporated to dryness to yield the de-esterified product, 7-[2-(2-thienyl)acetamido]-3-methylsulfonyloxy-3-cephem-4-carboxylic acid.

N.M.R. (acetone $d_6$) delta values: 3.33 (s, 3H, methyl); 3.50–4.00 (m, 4H, two $CH_2$); 5.10 (d, 1H, $C_6H$); 5.88 (d, 1H, $C_7H$); 6.80–7.40 (m, 3H, thiophene).
I.R. (KBr) 1795, 1175 cm$^{-1}$
U.V. (ethanol) $\lambda$ max 265 m$\mu$. (shoulder)
Elecrometric titration (80 percent aqueous methyl cellusolve) pKa 3.9.

EXAMPLE 11

7-[2-(2-Thienyl)acetamido]-3-(p-toluenesulfonyloxy)-3-cephem-4-carboxylic acid.

To a solution of 9.5 g. (20 mmole) of p-nitrobenzyl 7-[2-(2-thienyl)acetamido]-3-hydroxy-3-cephem-4-carboxylate in 30 ml. of DMAC and 30 ml. of propylene oxide maintained at ice-bath temperature were added 4.2 g. (22 mmole, 1.1 equivalents) of p-toluenesulfonyl chloride. The reaction mixture was stirred at ice-bath temperature for about 15 hours and then for about 3 hours at room temperature. Thereafter, the reaction mixture was evaporated to remove excess propylene oxide and the concentrate was dissolved in ethyl acetate. The solution was washed with a saturated sodium chloride solution and dried. Evaporation of the dried solution under reduced pressure afford the crude tosylate ester as a dry residue. The residue was dissolved in ethyl acetate and chromatographed over water-deactivated silica gel (Woelm silica gel, 10 percent water deactivated) packed in a glass column. The column was eluted with 45 percent by volume of hexane in ethyl acetate. Four fractions of approximately 100 ml. volume were collected. Fractions 2 and 3 were combined and evaporated under reduced pressure to yield 4.75 g. of p-nitrobenzyl 7-[2-(2-thienyl)acetamido]-3-(p-toluenesulfonyloxy)-3-cephem-4-carboxylate mixed with the corresponding 2-cephem isomer.

To a solution of 1.26 g. of the isomeric mixture in 20 ml. of methylene chloride maintained at ice-bath temperature was added a solution of 0.4 g. of m-chloroperbenzoic acid in 20 ml. of methylene chloride. The mixture was stirred for 40 minutes and was evaporated to dryness. The residue was triturated with iso-propanol, filtered, washed with ether and dried to yield 1.1 g. of product, p-nitrobenzyl, 7-[2-(2-thienyl)acetamido]-3-(p-toluenesulfonyloxy)-3-cephem-4-carboxylate sulfoxide. Percent elemental composition of the sulfoxide product, calculated for $C_{27}H_{23}N_3O_{10}S_3$, was as follows:

Theory: C, 50.23; H, 3.59; N, 6.51; Found: C, 49.98; H, 3.30; N, 6.53.

The $\Delta^3$-cephem sulfoxide was reduced to the $\Delta^3$-cephem sulfide as follows:

To a solution of 1.0 g. of the sulfoxide in 25 ml. of acetonitrile containing 5 ml. of DMF maintained at ice-bath temperature were added 0.157 g. of phosphorus tribromide with stirring. The reaction mixture was stirred for 1 hour in the cold. Ethyl acetate and a saturated aqueous sodium chloride solution were added to the mixture. The product was extracted with the ethyl acetate and the organic layer was washed 3 times with a saturated sodium chloride solution. The organic phase was dried and evaporated to yield 1.1 g. of the product, p-nitrobenzyl 7-[2-(2-thienyl)acetamido]-3-(p-toluenesulfonyloxy)-3-cephem-4-carboxylate.

The above product was hydrogenated over prereduced 5 percent palladium on carbon catalyst in methanol-THF by the procedure described in Example 10 to provide the free carboxylic acid product, 7-[2-(2-thienyl)acetamido]-3-(p-toluenesulfonyloxy)-3-cephem-4-carboxylic acid.

N.M.R. (CDCl$_3$) delta values: 2.47 (s, 3H, methyl); 3.40–4.10 (m, 4H, $C_2$ and side chain $CH_2$); 5.05 (d, 2H, $C_6H$); 5.80 (q, 1H, $C_7$—H); 6.85–7.38 (m, 3H, thiophene); 7.61 (q, 4H, phenyl).
I.R. (CHCl$_3$) 1790, 1380, 1170 cm$^{-1}$
Electrometric titration (80 percent aqueous methyl cellosolve) pKa 4.4.
U.V. (ethanol) $\lambda$ max 265 m$\mu$. (shoulder).
Electrometric titration (80 percent aqueous methyl cellosolve) pKa 4.25.

EXAMPLE 12

To a solution of 11.1 g. of p-nitrobenzyl 7-amino-3-hydroxy-3-cephem-4-carboxylate hydrochloride in 500 ml. of tetrahydrofuran were added 15.1 g. of sodium bisulfite. The mixture was stirred at room temperature for 1 hour and 6.4 g. of N-(t-butyloxycarbonyl)-phenylglycine and 6.25 g. of N-ethoxycarbonyl-2-ethoxy-1,2-dihydroquinoline (EEDQ) were then added. The reaction mixture was stirred at room temperature for 7 hours after which the mixture was evaporated to remove tetrahydrofuran. The concentrate was dissolved in ethyl acetate and the solution was washed consecutively with a solution of sodium bicarbonate, dilute hydrochloric acid and a saturated sodium chloride solution and was dried. The dried solution was evaporated to dryness to yield 11.14 g. of p-nitrobenzyl 7-(N-t-butyloxycarbonyl-D-phenylgylcylamido)-3-hydroxy-3-cephem-4-carboxylate.

To a solution of 11.14 g. of the above product in 50 ml. of DMAC containing 25 ml. of propylene oxide were added at room temperature 1.47 ml. of methanesulfonyl chloride. After the mixture was stirred for about 3 hours, an additional 1.47 ml. of methanesulfonyl were added and the mixture was stirred for an additional 15 hours. The reaction mixture was diluted with ethyl acetate and the solution extracted 4 times with a saturated solution of sodium chloride. The washed organic phase was dried and evaporated to dryness to yield crude reaction product, p-nitrobenzyl 7-(N-t-butyloxycarbonyl-D-phenylglycylamido)-3-methylsulfonyloxy-3 cephem-4-carboxylate. The product was purified by dissolution in methylene chloride and precipitation from solution on dilution with hexane. The purified product, 8.09 g. was filtered and dried.

The p-nitrobenzyl ester group was removed by hydrogenation of the product over pre-reduced 5 percent palladium on carbon by the method described in Example 10, to yield 4.21 g. of the free acid.

The free acid obtained, 1.545 g. was dissolved in 3 ml. of dry acetonitrile and 1.7 g. of p-toluenesulfonic acid were added. The reaction mixture was stirred overnight at room temperature. Water was added to the mixture and the pH adjusted to 5.0 with a solution of sodium bicarbonate. The mixture was then evaporated to remove acetonitrile and the aqueous residue was filtered. The pH of the filtrate was adjusted to pH 4.0 and was then freeze dried. The freeze dried mixture was triturated with acetone and filtered. The solid was dissolved in 15 ml. of water and about 5 ml. of acetone were added to the solution at ice-bath temperature. The product, 7-(D-phenylglycylamido)-3-methylsulfonyloxy)-3-cephem-4-carboxylic acid, crystallized from the cold solution and was filtered, washed with cold water and with acetone and was dried to provide 143 mg.

Percent elemental composition for $C_{16}H_{17}N_3O_7S_2$: Theory: C, 44.92; H, 4.01; N, 9.83; Found: C, 44.13; H, 4.24; N, 9.26.

Electrometric titration in 80 percent aqueous methyl cellosolve pKa 3.6 and 6.75

I.R. (mull) 1780, 1360, and 1178 cm$^{-1}$

U.V. (pH 6 buffer) λ max 261 mμ. ($\epsilon$=8400)

N.M.R. (DMSO d$_6$) delta values: 3.28 (s, 3H, methyl); 3.55 (q, 2H, $C_2$—$CH_2$); 4.92–5.1 (m, 2H, $C_6$H and CH of side chain); 5.68 (q, 1H, $C_7$–H); 7.48 (m, 5H, phenyl).

C. Preparation of 3-Thio Substituted-3-Cephem Compounds

EXAMPLE 13 p-Nitrobenzyl 7-[2-(2-thienyl)acetamido]-3-[(1-methyl-1H-tetrazole-5-yl)thio]-3-cephem-4-carboxylate.

To a solution of 4.9 g. (10 mM) of p-nitrobenzyl 7-[2-(2-thienyl)acetamido]-3-chloro-3-cephem-4-carboxylate and 10 mM of 1-methyl-1H-tetrazole-5-thiol in 60 ml. of dimethyl sulfoxide (dried with molecular sieve) were added 4.16 g. (40 mM) of sodium bisulfite in 4 equal portions at hourly intervals. The reaction mixture was stirred at room temperature for 5 hours and was then poured into a mixture of water and ethyl acetate with stirring. The organic layer was separated, extracted several times with water, dried over magnesium sulfate, and evaporated to dryness under vacuum. The amorphous residue was triturated with diethyl ether and chromatographed over a column packed with silica gel. The eluted reaction product was a mixture of the Δ$^2$ and Δ$^3$ cephem product with some unreacted starting material.

One gram (1.75 mM) of the mixture, p-nitrobenzyl 7-[2-(2-thienyl)acetamido]-3-[(1-methyl-1H-tetrazole-5-yl)thio]-2- and -3-cephem-4-carboxylate was suspended in 60 ml. of isopropanol and 10 ml. of methylene chloride. The suspension was cooled in an ice-water bath and 370 mg. (2.1 mM) of m-chloroperbenzoic acid were added to the cold suspension. The reaction mixture was stirred in the cold for 3 hours and then at room temperature for about 2 hours. The reaction mixture was evaporated to dryness under vacuum and the residue dissolved in a mixture of ethyl acetate and water. The organic layer was separated, washed with water, dried over magnesium sulfate, and evaporated to dryness. The amorphous residue was triturated with diethyl ether to effect crystallization of the product, p-nitrobenzyl 7-[2-(2-thienyl)acetamido]-3-[(1-methyl-1H-tetrazole-5-yl)thio]-3-cephem-4-carboxylate sulfoxide. One gram of the crystalline product was obtained.

Elemental analysis calculated for $C_{22}H_{19}N_7O_7S_3$: Theory: C, 44.82; H, 3.25; N, 16.63; S, 16.31; Found: C, 44.68; H, 3.04; N, 16.41; S, 16.57.

One gram (1.7 mM) of the above sulfoxide 3-cephem p-nitrobenzyl ester was dissolved in 10 ml. of dry dimethylformamide (molecular sieve dried) and the solution was cooled in an ice-water bath. To the cold solution were added with stirring 700 mg. (5.1 mM) of phosphorus trichloride. The mixture was stirred for 15 minutes and was poured into a mixture of ethyl acetate and water. The organic phase was separated, washed several times with water, dried and evaporated to dryness under vacuum to yield 800 mg. (82 percent yield) of the sulfoxide reduction product, p-nitrobenzyl 7-[2-(2-thienyl)acetamido]-3-[(1-methyl-1H-tetrazole-5-yl)thio]-3-cephem-4-carboxylate.

N.M.R. (CDCl$_3$) showed signals at 6.4 (ABq, 2H, $C_2$—$H_2$), 6.09 (s, 2H, $\alpha CH_2$), 5.88 (s, 3H, tetrazole $CH_3$), 4.86 (d, 1H, $C_6$—H), 4.55 (s, 2H, ester $CH_2$), 4.08 (q, 1H, $C_7$—H), and 3.05–1.62 (m, 7H, aromatic H) tau.

EXAMPLE 14

7-[2-(2-Thienyl)acetamido]-3-[(1-methyl-1H-tetrazole-5-yl)thio]-3-cephem-4-carboxylic acid.

To a solution of 500 mg. (0.87 mM) of p-nitrobenzyl 7-[2-(2-thienyl)acetamido]-3-[(1-methyl-1H-tetrazole-5-yl)thio]-3-cephem-4-carboxylate in 5 ml. of tetrahydrofuran and 75 ml. of methanol were added 500 mg. of 5% palladium on carbon. The catalyst was prereduced in 15 ml. of ethyl alcohol under 50 psi of hydrogen for 30 minutes at room temperature prior to use.

The mixture was hydrogenated at room temperature for one-hour under 50 psi of hydrogen. The catalyst was filtered and washed on the filter with tetrahydrofuran and methanol and the washes were combined with the filtrate. The filtrate was evaporated to dryness under vacuum and the residue was dissolved in a mixture of ethyl acetate and water. The pH of the mixture was adjusted to 6.7 with 1N sodium hydroxide and the aqueous layer was separated and washed with ethyl acetate. The aqueous phase was layered with ethyl acetate and then was acidified to pH 2.5 with 1N hydrochloric acid. The ethyl acetate layer was separated, washed with water, dried and evaporated to dryness under vacuum. The residue was triturated with diethyl ether and vacuum dried to yield 180 mg. (46% yield) of 7-[2-(2-thienyl)acetamido]-3-[(1-methyl-1H-tetrazole-5-yl)thio]-3-cephem-4-carboxylic acid.

The product was shown to be one-spot material on a silica gel thin layer chromatogram using chloroform-methanol (7:3 v:v) for elution.

Electrometric titration of the product in water showed one titratable group having a pKa of 3.5.

The ultraviolet absorption spectrum of the product showed maxima at 270 mμ ($\epsilon$=7400) and 233 mμ ($\epsilon$=12,200).

Elemental analysis calculated for $C_{15}H_{14}N_6O_4S_3$: Theory: C, 41.09; H, 3.22; N, 19.17; Found: C, 40.84; H, 3.44; N, 19.09.

EXAMPLE 15 p-Nitrobenzyl 7-[D-2-(t-butyloxycarbamido)-2-phenylacetamido]-3-[(5-methyl-1,3,4-thiadiazol-2-yl)thio]-3-(and -2-)cephem-4-carboxylate.

To a solution of 6 g. (10 mM) of p-nitrobenzyl 7-[D-2-(t-butyloxycarbamido)-2-phenylacetamido]-3-chloro-3-cephem-4-carboxylate and 5.3 g. (40 mM) of 5-methyl-1,3,4-thiadiazole-2-yl-thiol in 60 ml. of molecular sieve-dried dimethylsulfoxide was added 4.16 g. (40 mM) of sodium bisulfite in 4 equal portions at hourly intervals. The reaction mixture was stirred for 5 hours and was then poured into a mixture of ethyl acetate and water. The organic phase was separated, washed with water, dried and evaporated to dryness under vacuum. The crude product was purified by crystallization from a mixture of 100 ml. of ethyl acetate, 200 ml. of diethyl ether and 100 ml. of petroleum ether (Skellysolve B) to yield 3 g. (43 percent yield) of the crystalline product as a mixture of the $\Delta^2$ and $\Delta^3$ cephem isomers.

Elemental analysis calculated for $C_{30}H_{30}N_6O_8S_3$: Theory: C, 51.56; H, 4.33; N, 12.03; Found: C, 51.36; H, 4.51; N, 11.75.

EXAMPLE 16 p-Nitrobenzyl 7-[D-2-(t-butyloxycarbamido)-2-phenylacetamido]-3-[(5-methyl-1,3,4-thiadiazole-2-yl)thio]-3-(-2-)cephem-4-carboxylate, 2 g. (2.9 mM), prepared as described by the preceding Example was hydrogenated over prereduced 5 percent palladium on carbon in a mixture of methanol and tetrahydrofuran. The reduction mixture was filtered, the filtrate evaporated to dryness, and the residue crystallized by trituration with diethyl ether containing a trace of ethyl formate to yield 821 mg. (51 percent yield) of the deesterified product, 7-[D-2-(t-butyloxycarbamido)-2-phenylacetamido]-3-[(5-methyl-1,3,4-thiadiazole-2-yl)thio]-3-(-2-)cephem-4-carboxylic acid.

Elemental analysis calculated for $C_{23}H_{25}N_5O_6S_3$: Theory: C, 49.01; H, 4.47; N, 12.42; S, 17.07; Found: C, 49.13; H, 4.73; N, 12.30; S, 16.80.

The product was dissolved in acetonitrile containing 2 molar equivalents of p-toluenesulfonic acid with respect to the cephalosporin and the solution was stirred at room temperature for about 15 hours. The mixture was diluted with water and the pH adjusted to about pH 5 with triethylamine. The product, 7-(D-phenylglycylamido)-3-[(5-methyl-1,3,4-thiadiazole-2-yl)thio]-3-(-2-)cephem-4-carboxylic acid, precipitated as a crystalline solid.

EXAMPLE 17 p-Nitrobenzyl 7-[D-2-(t-butyloxycarbamido)-2-phenylacetamido]-3-[(1-methyl-1H-tetrazole-5-yl)thio]-3-cephem-4-carboxylate.

To a solution of 603 mg. (1 mM) of p-nitrobenzyl 7-[D-2-(t-butyloxycarbamido)-2-phenylacetamido]-3-chloro-3-cephem-4-carboxylate and 464 mg. (4 mM) of 1-methyl-1H-tetrazole-5-ylthiol in 6 ml. of molecular sieve-dried dimethylsulfoxide were added 416 mg. (4 mM) of sodium bisulfite in four equal portions at hourly intervals. The reaction mixture was stirred at room temperature for 5 hours and was then poured into a mixture of ethyl acetate and water. The organic phase was separated, washed repeatedly with water, dried and evaporated to dryness under vacuum. The amorphous residue crystallized when triturated with diethyl ether to provide 450 mg. (66 percent yield) of the crystalline product.

The infrared spectrum of the product in chloroform showed absorption maxima at 2.93 (amide NH), 5.59 (broad, β-lactam and ester carbonyl absorption) and 5.92 (broad amide II band) microns.

The ultraviolet absorption of the product in acetonitrile showed maximum at 265 m$\mu$ ($\epsilon$=17,000).

Elemental analysis calculated for $C_{29}H_{30}N_8O_8S_2$: Theory: C, 51.02; H, 4.43; N, 16.41; Found: C, 50.82; H, 4.40; N, 16.51.

EXAMPLE 18

7-(D-Phenylglycylamido)-3-[(1-methyl-1H-tetrazole-5-yl)thio]-3-cephem-4-carboxylic acid.

The product obtained as described by the preceding Example 2 g. (2.9 mM) was dissolved in 150 ml. of methyl alcohol containing 10 ml. of tetrahydrofuran and hydrogenated under 50 psi of hydrogen for one hour in the presence of 2 g. of prereduced 5 percent palladium on carbon. The catalyst was filtered, washed on the filter with tetrahydrofuran followed by methyl alcohol and the washings were combined with the filtrate. The filtrate was evaporated to dryness under vacuum and the residue dissolved in an ethyl acetate-water mixture. The pH of the mixture wad adjusted to about pH 7 with 1N sodium hydroxyde. The aqueous layer was separated, washed with ethyl acetate, layered with fresh ethyl acetate, and acidified to pH 1.5 with 1N hydrochloric acid. The ethyl acetate layer was separated, washed with water, dried over magnesium sulfate and evaporated to dryness. The crude deesterified product, 1.1 g. (68 percent yield) was obtained crystalline from diethyl ether containing a trace of ethyl formate.

The ultraviolet absorption spectrum of the product in acetonitrile showed a maximum at 280 m$\mu$ ($\epsilon$=10,200).

Elemental analysis calculated for $C_{22}H_{25}N_7O_6S_2\cdot 1/2$ $H_2O$: Theory: C, 47.19; H, 4.71; N, 17.62; Found: C, 47.05; H, 4.79; N, 17.03.

The product 7-[D-2-(t-butyloxycarbamido)-2-phenylacetamido]-3-[(1-methyl-1H-tetrazole-5-yl)thio]-3-cephem-4-carboxylic acid, 740 mg. (1.46 mM), was dissolved in 14 ml. of acetonitrile containing 610 mg. (3.2 mM) of p-toluenesulfonic acid. The mixture was stirred at room temperature overnight and was diluted with 1.4 ml. of water. The pH of the solution was adjusted to pH 5 with triethylamine. The product, 7-(D-phenylglycylamido)-3-[(1-methyl-1H-tetrazole-5-yl)thio]-3-cephem-4-carboxylic acid, precipitated as a white cyrstalline solid. The product was filtered, washed with acetonitrile and dried under vacuum to yield 440 mg. (65 percent yield).

Electrometric tritration of the product in 66 percent dimethylformamide showed the presence of two titratable groups having pKa values at 3.75 (COOH) and 7.0. The apparent molecular weight calculated from titration data was 468. The calculated molecular weight is 466.

The ultraviolet absorption spectrum of the product in pH 6 phosphate buffer showed a maximum at 275 m$\mu$ ($\epsilon$=8,900).

The nuclear magnetic resonance spectrum ($D_2O$—DCl) showed signals at 6.70 (ABq, 2H, C—H$_2$), 5.91 (s, 3H, tetrazole CH$_3$), 4.78 (d, 1H, C$_6$—H), 4.09 (d, 1H, C$_7$—H) and 2.36 (s, 5H, aromatic H).

Elemental analysis calculated for C$_{17}$H$_{19}$N$_7$O$_5$S$_2$: Theory: C, 43.86; H, 4.11; N, 21.06; S, 13.78; Found: C, 43.65; H, 3.89; N, 20.78; S, 13.52.

EXAMPLE 19 p-Nitrobenzyl 7-[2-(2-thienyl)acetamido]-3-methylthio-3-cephem-4-carboxylate.

A solution of 157 mg. (0.25 mM) of p-nitrobenzyl 7-[2-(2-thienyl)acetamido]-3-p-toluenesulfonyloxy-3-cephem-4-carboxylate in 8 ml. of dimethylformamide was cooled to about −41° C. in an acetonitrile-dry ice bath and was added to a solution of 0.014 ml. (0.25 mM) of methyl mercaptan in 4 ml. of dimethylformamide containing 12 mg. of sodium hydride maintained at a temperature of about −45° C. The reaction mixture was stirred for 1.5 hours and 1 ml. of glacial acetic acid was added. The reaction mixture was evaporated and the residue extracted with ethyl acetate. The extract was washed with a saturated sodium chloride solution and with 5 percent hydrochloric acid. The washed extract was dried over magnesium sulfate and then evaporated to dryness to yield an oil. The oil was dried overnight under vacuum and the yellow precipitate (180 mg.) which formed was filtered. The precipitate of crude product was purified by preparative thin layer chromatography on silica gel coated plates. The crude product was spotted on the plates as a chloroform solution and the plates were developed with a 7:3, v:v mixture of benzene:ethyl acetate.

EXAMPLE 20 p-Nitrobenzyl 7-[2-(2-thienyl)acetamido]-3-phenylthio-3-cephem-4-carboxylate.

To 6 ml. of dry dimethylformamide containing 12 mg. of sodium hydride were added 0.026 ml. of thiophenol and the solution obtained was cooled to about −41° C. To the cold solution was added a solution of 123 mg. of p-nitrobenzyl 7-[2-(2-thienyl)acetamido]-3-chloro-3-cephem-4-carboxylate in 6 ml. of dimethylformamide precooled to −41° C. The reaction mixture was stirred in the cold for 2.5 hours. The reaction mixture was poured into 200 ml. of ethyl acetate and the solution was washed with 5 percent hydrochloric acid and brine and dried over magnesium sulfate. The dried ethyl acetate solution was evaporated to dryness to yield 141 mg. of crude product. The product was purified via preparative thin layer chromatography on silica gel plates developed with 7:3, v:v, benzene:ethyl acetate. The product was extracted from the chromatograms with a mixture of chloroform, ethyl acetate, and acetic anhydride, and the extract was filtered and evaporated to yield 50 mg. of the purified product.

EXAMPLE 21 p-Nitrobenzyl 7-[2-(2-thienyl)acetamido]-3-(4-t-butylphenylthio)-3-cephem-4-carboxylate.

By following the procedures described by the preceding example for the preparation of the 3-phenylthio-3-cephem ester, 123 mg. of p-nitrobenzyl 7-[2-(2-thienyl)acetamido]-3-chloro-3-cephem-4-carboxylate was reacted for 2 hours at −41° C. with 4-t-butylthiophenol in dimethylformamide containing sodium hydride to yield 205 mg. of crude p-nitrobenzyl 7-[2-(2-thienyl)acetamido]-3-(4-t-butylphenylthio)-3-cephem-4-carboxylate contaminated with the 3-chloro-3-cephem starting material and with 4-t-butylthiophenol. The crude product, 195 mg. of the above mixture, was purified by preparative thin layer chromatography on silica gel coated plates developed with benzene:ethyl acetate, 7:3, v:v to yield 76 mg. The nuclear magnetic resonance spectrum run in deuterated chloroform and the infrared absorption spectrum of the purified product were in agreement with the structure of the product. The mass spectrum of the purified product gave a parent ion at 623 m/e.

EXAMPLE 22 p-Nitrobenzyl 7-[2-(2-thienyl)acetamido]-3-(4-fluorophenylthio)-3-cephem-4-carboxylate.

By employing the reaction conditions, reagents and solvents used in the preceding examples, 123 mg. of the 3-chloro-3-cephem ester was reacted with 32 mg. of 4-fluorothiophenol to yield 143 mg. of crude product. The crude product was purified by preparative thin layer chromatography over silica gel developed with benzene:ethyl acetate (7:3, v:v). The separated product was extracted from the silica gel with acetic acid to yield 56 mg. of the purified product. The mass spectrum of the product showed a parent ion at 585 m/e.

We claim:
1. A cephalosporin compound of the formula

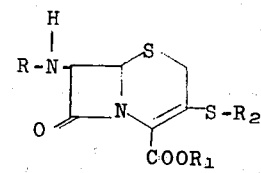

wherein R is hydrogen or an acyl group derived from a carboxylic acid and represented by the formula

wherein R' is C$_1$–C$_6$ alkyl, C$_1$–C$_3$ haloalkyl, C$_1$–C$_3$ cyanoalkyl, phenyl, mono- or di-methylphenyl, mono- or di-hydroxyphenyl, mono- or di-halophenyl, mono- or di-nitrophenyl, mono- or di-aminophenyl, and mono- or di-methoxyphenyl; or R' is a group of the formula

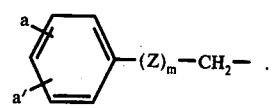

wherein $a$ and $a'$ independently are hydrogen, C$_1$–C$_4$ lower alkyl, C$_1$–C$_4$ lower alkoxy, halogen, hydroxy, nitro, amino, or carboxy;
Z is O or S; and
$m$ is 0 or 1;
or R' is a group of the formula

wherein P is 2-thienyl, 3-thienyl, phenyl or a substituted phenyl group of the formula

wherein $a$ and $a'$ are as defined above, Q is hydroxyl, formyloxy, acetoxy, carboxy, sulfo, amino, or amino protected by t-butyloxycarbonyl, 2,2,2-trichloroethoxycarbonyl, or the group of the formula

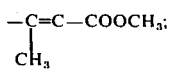

or R' is a group of the formula $$R''-CH_2-$$

wherein R'' is 2-thienyl, 3-thienyl, 2-furyl, [2-oxazyl, 2-thiazyl, or 1 tetrazyl] 2-oxazolyl, 2-thiazolyl, or 1-tetrazolyl;

$R_1$ is hydrogen, benzyl, 4-methoxybenzyl, 4-nitrobenzyl, diphenylmethyl, 2,2,2-trichloroethyl, or t-butyl;

$R_2$ is a heterocyclic ring selected from the group consisting of

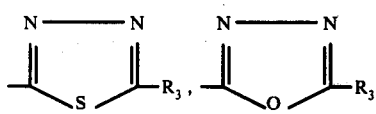

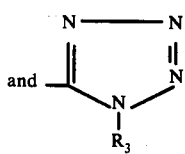

wherein $R_3$ is $C_1$–$C_3$ lower alkyl;

and where $R_1$ is hydrogen, the pharmaceutically acceptable non-toxic salts thereof.

2. The compound of claim 1 wherein R' is a group of the formula

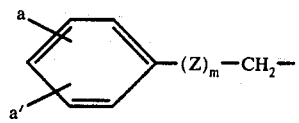

3. The compound of claim 1 wherein R' is a group of the formula $$R''-CH_2-$$

4. The compound of claim 3 wherein R'' is 2-thienyl and $-S-R_2$ is a heterocyclic thio-substituted ring selected from the group consisting of 5-methyl-1,3,4-thiadiazole-2-ylthio, 5-methyl-1,3,4-oxadiazole-2-ylthio and 1-methyl-1H-tetrazole-5-ylthio.

5. The compound of claim 4, said compound being 7-[2-(2-thienyl)acetamido]-3-(1-methyl-1H-tetrazole-5-ylthio)-3-cephem-4-carboxylic acid.

6. The p-nitrobenzyl ester of the compound of claim 5.

7. The compound of claim 1 wherein R' is a group of the formula

8. The compound of claim 7 wherein P is phenyl or substituted phenyl.

9. The compound of claim 8 wherein Q is amino or amino protected by t-butyloxycarbonyl, 2,2,2-trichloroethoxycarbonyl or

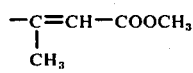

and $-S-R_2$ is a heterocyclic thio substituted ring selected from the group consisting of 5-methyl-1,3,4-thiadiazole-2-ylthio, 5-methyl-1,3,4-oxadiazole-2-ylthio and 1-methyl-1H-tetrazole-5-ylthio.

10. The compound of claim 9, said compound being p-nitrobenzyl 7-[D-2-(t-butyloxycarbamido)-2-phenylacetamido]-3-[(1-methyl-1H-tetrazole-5-yl)thio]-3-cephem-4-carboxylate.

11. The compound of claim 9, said compound being 7-(D-phenylglycylamido)-3-[(1-methyl-1H-tetrazole-5-yl)thio]-3-cephem-4-carboxylic acid.

12. The compound of claim 9, said compound being p-nitrobenzyl 7-[D-2-(t-butyloxycarbamido)-2-phenylacetamido]-3-[(5-methyl-1,3,4-thiadiazole-2-yl)thio]-3-cephem-4-carboxylate.

13. The compound of claim 9, said compound being 7-(D-phenylglycylamido)-3-[(5-methyl-1,3,4-thiadiazole-2-yl)thio]-3-cephem-4-carboxylic acid.

* * * * *